United States Patent [19]

Kovacevic et al.

[11] Patent Number: 4,977,089

[45] Date of Patent: Dec. 11, 1990

[54] VECTOR COMPRISING SIGNAL PEPTIDE-ENCODING DNA FOR USE IN BACILLUS AND OTHER MICROORGANISMS

[75] Inventors: Steven Kovacevic; James R. Miller, both of Indianapolis, Ind.; Loraine E. Veal, Phoenix, Ariz.; John S. Wood, Indianapolis, Ind.

[73] Assignee: Eli Lilly and Company, Indianapolis, Ind.

[21] Appl. No.: 10,245

[22] Filed: Jan. 30, 1987

[51] Int. Cl.$^5$ .................. C12N 15/70; C12N 15/75
[52] U.S. Cl. ................ 435/252.31; 435/172.3; 435/252.33; 435/320; 935/11; 935/29; 935/73; 935/74
[58] Field of Search .............. 435/68, 172.3, 253, 435/839, 320, 252.31, 252.33; 935/11, 29, 73, 74

[56] References Cited

U.S. PATENT DOCUMENTS

| | | | |
|---|---|---|---|
| 4,503,142 | 3/1985 | Berman | 435/6 |
| 4,559,300 | 12/1985 | Kovacevic | 435/68 |
| 4,601,980 | 7/1986 | Goeddel | 435/70 |
| 4,666,847 | 5/1987 | Alford | 435/253 |
| 4,740,461 | 4/1988 | Kaufman | 435/68 |
| 4,783,405 | 11/1988 | Kovacevic | 435/68 |
| 4,801,536 | 1/1989 | Stahl | 435/68 |
| 4,801,537 | 1/1989 | Nagakajan | 435/68 |

FOREIGN PATENT DOCUMENTS 0036259 9/1981 European Pat. Off. .
0057976 3/1982 European Pat. Off. .

OTHER PUBLICATIONS

Smith, Robert A. et al., Science, 20, Sep. 1985, pp. 1219–1223.
Perlman, D. et al., 1986, PNAS 83(14), 5033–5037.
Watson, J. D. et al., 1983, Recombinant DNA, W. H. Freeman & Co., N.Y., p. 86.
Lovett et al., 1979, Meth.—Enzymol., 68:342.
Shortle, 27/Nov. 1985, Genebank Accession, A00790, Text entry for Sequence.
Moran C. et al., 1982, Mol Gen Genetics, 186: 336–346.
Shortle, 1983, Gene 22:181.
Palva, 1982, Gene 19:81.
Palva et al., 1982, Proc. Natl. Acad. Sci., U.S.A. 79:5582.
Mosbach et al., 1983, Nature 302:543.
Saunders et al., 1984, J. Bacteriology 157,718.
Fairweather et al., 1983, Infec. Immun. 41:1112.
Palva et al., 1983, Gene 22:229.
Band and Henner, 1984, DNA 3(1): 17–21.
Kovacevic et al., 1985, J. Bacteriol. 162(2): 521–528.
Miller et al., 1985, Poster Presented at the 3d Intl. Conference on Genetics and Biotechnology of Bacilli.
Neuberger et al., 1984, Nature 312: 604–608.

Primary Examiner—Richard A. Schwartz
Attorney, Agent, or Firm—Joseph A. Jones; Leroy Whitaker

[57] ABSTRACT

A novel promoter, ribosome-binding site-encoding DNA, and a number of signal peptide-encoding DNA sequences are described for use in Bacillus and other host cells. The compounds are useful in constructing expression vectors for use in Bacillus and other host cells and drive expression and secretion of proteins such as nuclease and human growth hormone. In addition, a general method for obtaining cells with increased abilities to express and secrete heterologous gene products is described.

24 Claims, 7 Drawing Sheets

VECTOR COMPRISING SIGNAL PEPTIDE-ENCODING DNA FOR USE IN BACILLUS AND OTHER MICROORGANISMS

SUMMARY OF THE INVENTION

The present invention concerns a novel promoter and ribosome-binding site-encoding DNA useful in Bacillus and other microorganisms. The novel promoter and ribosome-binding site-encoding DNA are especially useful when used with DNA that encodes a signal peptide, a relatively short sequence of amino acids that directs the host cell to secrete any polypeptide attached to the signal peptide. The present invention also provides a number of signal peptide-encoding DNA compounds that direct secretion of proteins in Bacillus.

The promoter, ribosome-binding site-encoding DNA, and signal peptide-encoding DNA of the present invention have been used to construct a variety of recombinant DNA expression vectors. A recombinant DNA vector is a segment of DNA that exists either freely-replicating in the cytoplasm or integrated into the genome of the host cell into which it has been transferred. An expression vector additionally encodes at least one polypeptide that is expressed by the host cells transformed with the vector. The expression vectors of the present invention code for the expression of such useful products as nuclease, proinsulin, and human growth hormone and can be readily modified to express virtually any polypeptide or protein.

The extremely limited ability of Bacillus to recognize transcription and translation signals presently available necessitates the development of new sequences that direct gene expression. Several early attempts at expression include the cloning and expression in B. subtilis of the B. licheniformis beta-lactamase gene (disclosed in European Patent Office Publication [of European Patent Application No. 81300858.8] No. 0036259) and the B. stearothermophilus and B. amyloliquefaciens α-amylase genes (respectively disclosed in European Patent Office Publication [of European Patent Application No. 82300158.1] No. 0057976 and Derwent Abstract [of Belgium Patent Application No. BE 891–659] No. 37323 E/19) Modifications of the B. subtilis veg promoter and translation signals (disclosed in United States Patent Application Ser. No. 654,437) are also useful for directing the expression of heterologous polypeptides in Bacillus. A polypeptide is heterologous with respect to a given host cell if that host cell does not express the polypeptide absent intervention with genetic engineering techniques. In addition, Palva et al. (Palva et al., 1983, Gene 22:229 and Palva et al., 1982, Proc. Natl. Acad. Sci. USA 79:5582) have succeeded in expressing and secreting foreign gene products in B. subtilis by using transcription, translation, and secretion signals from the B. amyloliquefaciens α-amylase gene. About 20 mg of E. coli βlactamase and 500 μg of human interferon per liter were obtained from the culture supernatants. Mosbach (Mosbach et al., 1983, Nature 302:543) has cloned and obtained expression of rat "proinsulin-like" activity at a low level of about 10 μg per liter.

Saunders (Saunders et al., 1984, J. Bacteriol. 157:718) reported that a Staphylococcus aureus β-lactamase was expressed as one percent of the total protein in B. subtilis. The β-lactamase protein, normally secreted in S. aureus, was not secreted but was cell-associated in B. subtilis. Also, Fairweather, (Fairweather et al., 1983, Infec. Immun. 41:1112) detected S. aureus α-hemolysin in B. subtilis supernatants.

Gene cloning and expression of products in Bacillus subtilis are highly advantageous since the organism is non-pathogenic, does not produce endotoxins, and can secrete gene products into the growth medium. In addition, B. subtilis has been extensively studied and is the archetype for genetic studies among Gram-positive microorganisms. The method and expression vectors of the present invention are particularly important because they allow for the commercial exploitation of these important advantages.

For purposes of the present invention, as disclosed and claimed herein, the following terms are as defined below.

Recombinant DNA Vector—any replicating or integrating agent, including but not limited to plasmids, comprising a DNA molecule to which one or more additional DNA segments can be or have been added.

Transformation—the introduction of DNA into a recipient host cell.

Transformant—a recipient host cell that has undergone transformation.

Restriction Fragment—any linear DNA generated by the action of one or more restriction enzymes.

Promoter—a DNA sequence that directs the transcription of DNA into messenger RNA (mRNA).

Translational Activating Sequence—a DNA sequence, which corresponds to the ribosome-binding site-encoding DNA and the nucleotide triplet that codes for the translational start codon, that directs the translation of mRNA into a polypeptide.

Functional Polypeptide—a recoverable bioactive entirely heterologous or homologous polypeptide or precursor, a recoverable bioactive polypeptide comprising a heterologous polypeptide and a portion or whole of a homologous polypeptide, or a recoverable bioinactive fusion polypeptide comprising a heterologous polypeptide and a bioinactivating homologous polypeptide which can be specifically cleaved.

Fused Gene Product—a recoverable heterologous polypeptide which is fused with a polypeptide or a portion or whole of a homologous protein.

Background of the Invention

Shortle, 1983, Gene 22:181, disclosed the nucleotide sequence of the staphylococcal nuclease gene but, due to the possibility of a variety of start sites did not suggest where translation of the nuclease gene began. Kovacevic et al., 1985, J. Bacteriology 162(2):521, identified two potential promoters, the −10 and −35 regions which are underlined below, of the nuclease gene, the ribosome-binding site-encoding sequence (RBS) of the gene, and the translation start site of the nuclease gene, as depicted below.

```
              10         20         30
5'-TGTCTCGAT ATGATAGTCT GCAACGATTC ATGTTGTAGG 30        40         50         60        70
CTATTTAATT TTACAAATAA GGCTAAATAT ATAAGTTCTG ACACCTAAAA
```

```
         80              90             100           110         120
     TATAGAAAAT  ACATAAAAGT  AAGTATAGTT  ATTTTATTAT  AATTATTAAA 140             150            160           170         180
     TTTTTATTAA  TTAATTGTAA  AAATGTAGAA  TTATAATTAA  TTAACGTTTA
                    ─────              ─────          ───  ───
                    −35(1)             −35(2)         −10(1)

190             200            210           220         230           240
     ATATTAAAAT  TAACTAAAAA  GAAAGAGGTG  TTAGTT ATG ACA GAA TAC TTA
       ───                   ──────────         MET THR GLU TYR LEU
      −10(2)                    RBS                                5
```

```
         250            260            270            280
     TTA AGT GCT GGC ATA TGT ATG GCA ATT GTT TCA ATA TTA CTT ATA GGG
     LEU SER ALA GLY ILE CYS MET ALA ILE VAL SER ILE LEU LEU ILE GLY
                     10              15              20
```

```
         290            300            310            320            330
     ATG GCT ATC AGT ATT GTT TCG AAA GGG CAA TAC GCA AAG AGG TTT TTC
     MET ALA ILE SER ASN VAL SER LYS GLY GLN TYR ALA LYS ARG PHE PHE
                     25              30              35
```

```
         340            350            360            370            380
     TTT TTC GCT ACT AGT TGC TTA GTG TTA ACT TTA GTT GTA GTT TCA AGT
     PHE PHE ALA THR SER CYS LEU VAL LEU THR LEU VAL VAL VAL SER SER
                     40              45              50
```

```
         390            400            410            420            430
     CTA AGT AGC TCA GCA AAT GCA TCA CAA ACA GAT AAC GGC GTA AAT AGA
     LEU SER SER SER ALA ASN ALA SER GLN THR ASP ASN GLY VAL ASN ARG
      55              60   │                       65
                           └─▶first residue of nuclease B
```

```
         440            450            460            470            480
     AGT GGT TCT GAA GAT CCA ACA GTA TAT AGT GCA ACT TCA ACT AAA AAA
     SER GLY SER GLU ASP PRO THR VAL TYR SER ALA THR SER THR LYS LYS
      70              75              80  │                        85
                                          └─▶first residue of nuclease A
```

```
             490            500            510            520
         TTA CAT AAA GAA CCT GCG ACT TTA ATT AAA GCG ATT GAT GGT GAT ACG
         LEU HIS LYS GLU PRO ALA THR LEU ILE LYS ALA ILE ASP GLY ASP THR
                          90              95             100
```

```
         530            540            550            560            570
     GTT AAA TTA ATG TAC AAA GGT CAA CCA ATG ACA TTC AGA CTA TTA TTG
     VAL LYS LEU MET TYR LYS GLY GLN PRO MET THR PHE ARG LEU LEU LEU
                     105             110             115
```

```
         580            590            600            610            620
     GTT GAT ACA CCT GAA ACA AAG CAT CCT AAA AAA GGT GTA GAG AAA TAT
     VAL ASP THR PRO GLU THR LYS HIS PRO LYS LYS GLY VAL GLU LYS TYR
                     120             125             130
```

```
         630            640            650            660            670
     GGT CCT GAA GCA AGT GCA TTT ACG AAA AAA ATG GTA GAA AAT GCA AAG
     GLY PRO GLU ALA SER ALA PHE THR LYS LYS MET VAL GLU ASN ALA LYS
                     135             140             145
```

```
         680            690            700            710            720
     AAA ATT GAA GTC GAG TTT GAC AAA GGT CAA AGA ACT GAT AAA TAT GGA
     LYS ILE GLU VAL GLU PHE ASP LYS GLY GLN ARG THR ASP LYS TYR GLY
     150             155             160                            165
```

```
         730            740            750            760
     CGT GGC TTA GCG TAT ATT TAT GCT GAT GGA AAA ATG GTA AAC GAA GCT
     ARG GLY LEU ALA TYR ILE TYR ALA ASP GLY LYS MET VAL ASN GLU ALA
                     170             175             180
```

```
         770            780            790            800            810
     TTA GTT CGT CAA GGC TTG GCT AAA GTT GCT TAT GTT TAC AAA CCT AAC
     LEU VAL ARG GLN GLY LEU ALA LYS VAL ALA TYR VAL TYR LYS PRO ASN
                     185             190             195
```

```
         820            830            840            850            860
     AAT ACA CAT GAA CAA CAT TTA AGA AAA AGT GAA GCA CAA GCG AAA AAA
     ASN THR HIS GLU GLN HIS LEU ARG LYS SER GLU ALA GLN ALA LYS LYS
                     200             205             210
```

```
      870         880         890         900         910
GAG AAA TTA AAT ATT TGG AGC GAA GAC AAC GCT GAT TCA GGT CAA TAA
GLU LYS LEU ASN ILE TRP SER GLU ASP ASN ALA ASP SER GLY GLN
    215                 220                 225

920         930         940         950         960
TGC TCA TTG TAA AAG TGT CAC TGC TGC TAG TGG CAC TTT TAT AAT TTT 970         980
TAG ATC CTC TAC GCC GGA TCC-3'
```

Nucleotide and amino acid residues are abbreviated herein in as follows: (1) Nucleotides—A is deoxyadenyl, G is deoxyguanyl, C is deoxycytidyl, and T is thymidyl; and (2) Amino Acids—ALA is alanine, ARG is arginine, ASN is asparagine, ASP is aspartic acid, CYS is cysteine, GLN is glutamine, GLU is glutamic acid, GLY is glycine, HIS is histidine, ILE is isoleucine, LEU is leucine, LYS is lysine, MET is methionine, PHE is phenylalanine, PRO is proline, SER is serine, THR is threonine, TRP is tryptophan, TYR is tyrosine, and VAL is valine.

Kovacevic et al., demonstrated that the staphylococcal nuclease gene drove expression and secretion of nuclease in Bacillus host cells, even though the signal peptide (amino acid residues 1–60) was about twice as large as most Bacillus signal peptides. Nuclease undergoes rather complex processing in Bacillus and Staphylococcus host cells. First synthesized as the 228 amino acid residue protein depicted above, nuclease is secreted from the cell into the media to yield nuclease B, from which residues 1 (methionine) through 60 (alanine) have been cleaved. In the media, nuclease is further processed by removal of residues 61 (serine) through 79 (serine) to yield nuclease A. In addition, nuclease purified from the media of Bacillus or Staphylococcus cells that express the nuclease gene often lacks the amino-terminal alanine (residue 80) and threonine (residue 81) residues of nuclease A.

To achieve expression of staphylococcal nuclease in Bacillus host cells, Kovacevic et al. constructed plasmid pOW440, a plasmid that contains the replicon of plasmid pC194, a chloramphenicol resistance-conferring gene, and the staphylococcal nuclease gene. Plasmid pOW440 can be obtained from the Northern Regional Research Laboratories in *Bacillus subtilis* MI112 under the accession number NRRL B-15887. A restriction site and function map of plasmid pOW440 is presented in FIG. 1 of the accompanying drawings, and a protocol for the culture of *Bacillus subtilis* MI112/pOW440 host cells is presented in Example 1, below.

The present invention provides an improved staphylococcal nuclease promoter and signal peptide-encoding DNA. The improved promoter is smaller in size, more active, and more readily manipulable than the natural nuclease promoter. The improved signal peptide-encoding DNA is also smaller, and thus requires less of the cell's resources to synthesize, and more readily manipulable than the natural nuclease signal peptide-encoding DNA.

DETAILED DESCRIPTION OF THE INVENTION

The present invention comprises a DNA sequence that functions as a promoter in Bacillus and related host cells. The promoter is depicted below:

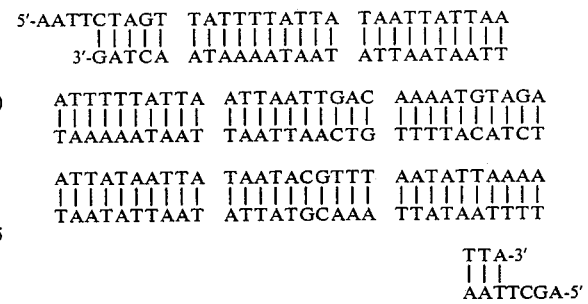

The promoter depicted above is shown with single-stranded DNA overlaps, one of which is characteristic of EcoRI cleavage, and the other, of HindIII cleavage. The promoter does not encode a ribosome-binding site, an important component of a translational activating sequence, but can readily be modified to encode such a sequence.

One preferred ribosome-binding site-encoding DNA sequence for use with the present promoter is depicted below:

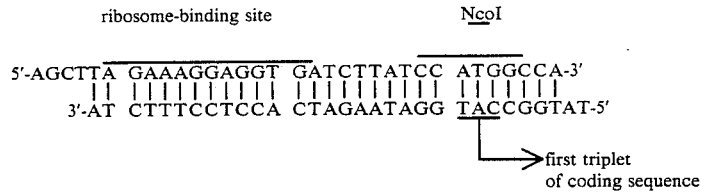

The ribosome-binding site-encoding DNA sequence depicted above has single-stranded DNA overlaps, one of which is characteristic of HindIII cleavage, and the other, of NdeI cleavage. Other ribosome-binding site-encoding DNA sequences can be used with the promoter of the present invention.

If secretion of the product encoded downstream of the promoter and ribosome-binding site-encoding DNA of the present invention is desired, the present invention provides a number of useful signal peptide encoding DNA fragments. The signal peptide of staphylococcal nuclease is depicted below:

An important aspect of the present invention concerns novel derivatives of the staphylococcal nuclease signal peptide and DNA that encodes these derivatives. These novel derivatives differ from the natural signal peptide or signal peptide-encoding DNA of staphylococcal nuclease in that one or more of the amino acid residues, or codons for such residues, from position 2 (threonine) up to position 28 (serine) are deleted to yield the novel signal peptide or signal peptide-encoding DNA.

Plasmid pOW350 exemplifies an expression vector of the present invention; a restriction site and function map

```
MET THR GLU TYR LEU LEU SER ALA GLY ILE CYS MET ALA ILE VAL
                      5                  10                  15
SER ILE LEU LEU ILE GLY MET ALA ILE SER ASN VAL SER LYS GLY
      20                  25                  30
GLN TYR ALA LYS ARG PHE PHE PHE PHE ALA THR SER CYS LEU VAL
      35                  40                  45
LEU THR LEU VAL VAL VAL SER SER LEU SER SER SER ALA ASN ALA
      50                  55                  60
```

Figure 2:
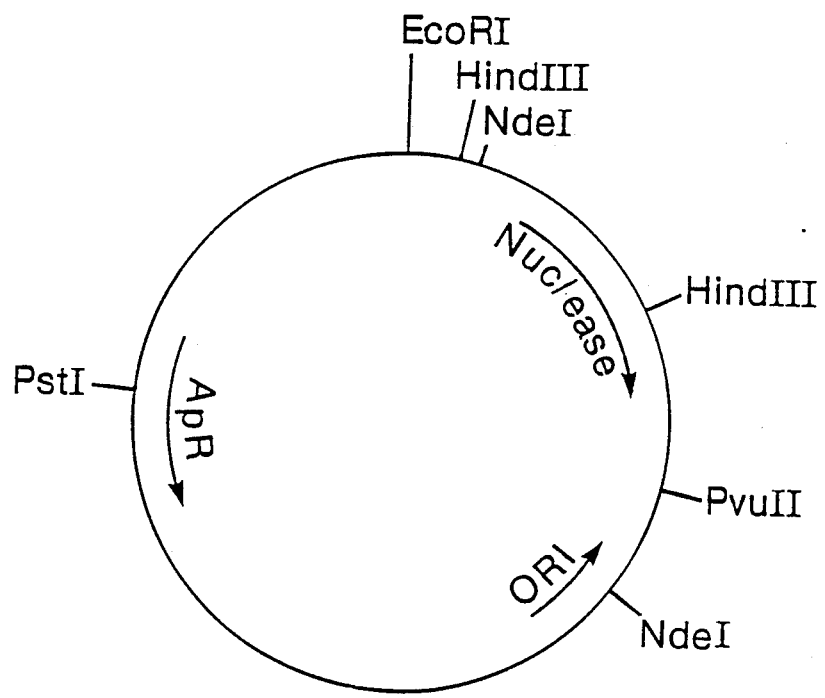
FIG. 2 is a restriction site and function map of plasmid pOW350.

A DNA sequence that encodes the signal peptide of staphylococcal nuclease can be synthesized readily or isolated from plasmid pOW440. Such a signal peptide-encoding DNA can then be inserted downstream of the promoter and ribosome-binding site DNA of the present invention and, upon translation, will direct secretion of any attached polypeptide from the host cell.

of plasmid pOW350 is presented in FIG. 2 of the accompanying drawings. Plasmid pOW350 encodes the novel promoter and ribosome-binding site-encoding DNA of the present invention together with one exemplification of the novel signal peptides of the present invention, all positioned to drive expression of staphylococcal nuclease, as represented below:

```
              10          20          30          40          50
5'-GAATTCTAGT TATTTTATTA TAATTATTAA ATTTTTATTA ATTAATTGAC 60          70          80          90   HindIII
   AAAATGTAGA ATTATAATTA TAATACGTTT AATATTAAAA TTAAGCTTA 100         110         120         130         140
   GAAAGGAGGT GATCTTATCC ATG GCC ATA TGT ATG GCA ATT GTT
                            MET ALA ILE CYS MET ALA ILE VAL
                                              5

150         160         170      AsuII      190
   TCA ATA TTA CTT ATA GGG ATG GCT ATC AGT AAT GTT TCG AAA GGG CAA
   SER ILE LEU LEU ILE GLY MET ALA ILE SER ASN VAL SER LYS GLY GLN
        10                  15                  20

200         210         220         230
   TAC GCA AAG AGG TTT TTC TTT TTC GCT ACT AGT TGC TTA GTG TTA ACT
   TYR ALA LYS ARG PHE PHE PHE PHE ALA THR SER CYS LEU VAL LEU THR
   25                  30                  35                  40

240         250         260         270         280
   TTA GTT GTA GTT TCA AGT CTA AGT AGC TCA GCA AAT GCA TCA CAA ACA
   LEU VAL VAL VAL SER SER LEU SER SER SER ALA ASN ALA SER GLN THR
                    45                  50                  55

290         300         310         320         330
   GAT AAC GGC GTA AAT AGA AGT GGT TCT GAA GAT CCA ACA GTA TAT AGT
   ASP ASN GLY VAL ASN ARG SER GLY SER GLU ASP PRO THR VAL TYR SER
            60                  65                  70

340         350         360         370         380
   GCA ACT TCA ACT AAA AAA TTA CAT AAA GAA CCT GCG ACT TTA ATT AAA
   ALA THR SER THR LYS LYS LEU HIS LYS GLU PRO ALA THR LEU ILE LYS
        75                  80                  85

390         400         410         420         430
   GCG ATT GAT GGT GAT ACG GTT AAA TTA ATG TAC AAA GGT CAA CCA ATG
   ALA ILE ASP GLY ASP THR VAL LYS LEU MET TYR LYS GLY GLN PRO MET
        90                  95                  100

440         450         460         470
   ACA TTC AGA CTA TTA TTG GTT GAT ACA CCT GAA ACA AAG CAT CCT AAA
   THR PHE ART LEU LEU LEU VAL ASP THR PRO GLU THR LYS HIS PRO LYS
   105         110         115         120
```

-continued

```
480         490         500         510         520
AAA GGT GTA GAG AAA TAT GGT CCT GAA GCA AGT GCA TTT ACG AAA AAA
LYS GLY VAL GLU LYS TYR GLY PRO GLU ALA SER ALA PHE THR LYS LYS
            125                     130                 135

530         540         550         560         570
ATG GTA GAA AAT GCA AAG AAA ATT GAA GTC GAG TTT GAC AAA GGT CAA
MET VAL GLU ASN ALA LYS LYS ILE GLU VAL GLU PHE ASP LYS GLY GLN
        140                 145                 150

580         590         600         610         620
AGA ACT GAT AAA TAT GGA CGT GGC TTA GCG TAT ATT TAT GCT GAT GGA
ARG THR ASP LYS TYR GLY ARG GLY LEU ALA TYR ILE TYR ALA ASP GLY
        155                 160                 165

630         640         650         600         670
AAA ATG GTA AAC GAA GCT TTA GTT CGT CAA GGC TTG GCT AAA GTT GCT
LYS MET VAL ASN GLU ALA LEU VAL ARG GLN GLY LEU ALA LYS VAL ALA
        170                 175                 180

680         690         700         710
TAT GTT TAC AAA CCT AAC AAT ACA CAT GAA CAA CAT TTA AGA AAA AGT
TYR VAL TYR LYS PRO ASN ASN THR HIS GLU GLN HIS LEU ARG LYS SER
185                 190                 195                 200

720         730         740         750         760
GAA GCA CAA GCG AAA AAA GAG AAA TTA AAT ATT TGG AGC GAA GAC AAC
GLU ALA GLN ALA LYS LYS GLU LYS LEU ASN ILE TRP SER GLU ASP ASN
            205                 210                 215

770         780         790         800         810
GCT GAT TCA GGT CAA TAA TGC TCA TTG TAA AAG TGT CAC TGC TGC TAG
ALA ASP SER GLY GLN
            220

XhoII
820         830                 850         860
TGG CAC TTT TAT AAT TTT TAG ATC CCT GGC CGT CGT TTT ACA ACG TCG 870         880         890         900         910
TGA CTG GGA AAA CCC GGG CGT TAC CAA ACT TAA TCG CCT TGC AGC ACA

PvuII
920             930         940         950
TCC CCC TTT CGC CAG CTG CCT CGC GCG TTT CGG TGA TGA CGG TGA AAA 960         970         980         990         1000
CCT CTG ACA CAT GCA GCT CCC GGA GAC GGT CAC AGC TTG TCT GTA AGC 1010        1020        1030        1040        1050
GGA TGC CGG GAG CAG ACA AGC CCG TCA GGG CGC GTC AGC GGG TGT TGG 1060        1070        1080        1090        1100
CGG GTG TCG GGC GCA GCC ATG ACC CAG TCA CGT AGC GAT AGC GGA GT 1110        1120        1130        1140        1150
GTA TAC TGG CTT AAC TAT GCG GCA TCA GAG CAG ATT GTA CTG AGA GTG

NdeI    1160
CAC CAT ATG-3'
```

The sequences from the XhoII to the PVUII sites originate from the E. coli lacZ gene, whereas the sequences from the PvuII to the NdeI site, and on around plasmid pOW350 up to the EcoRI site depicted at the start of the synthetic promoter, originate from plasmid pBR322.

The signal peptide encoded in plasmid pOW350 exemplifies the signal peptides of the present invention in that the DNA encoding amino acid residues 2 through 7 and 9 of the natural signal peptide of nuclease has been deleted in the construction of plasmid pOW350. Plasmid pOW350 can be obtained from E. coli K12 JA221/pOW350, a strain deposited with the Northern Regional Research Center under the accession number NRRL B-18119. A restriction site and function map of plasmid pOW350 is presented in FIG. 2 of the accompanying drawings. A procedure for isolating plasmid pOW350 from E. coli K12 JA221/pOW350 is presented in Example 2. Plasmid pOW350 drives expression and secretion of nuclease in E. coli host cells but contains no Bacillus replicon. To use plasmid pOW350 in Bacillus host cells, a Bacillus replicon can be added to the plasmid. A preferred Bacillus replicon is contained on plasmid pBC16, available from the Bacillus Genetic Stock Center, Ohio State University, Department of Microbiology, 484 W. 12th Avenue, Columbus, Ohio 43210, order number 1E9. Plasmid pBC16 contains two EcoRI restriction enzyme recognition sites. The larger EcoRI restriction fragment of plasmid pBC16 was inserted into plasmid pOW350 to yield plasmid pOW350-16. The construction protocol for plasmid pOW350-16 is described in Example 2, as well as a protocol for transforming Bacillus subtilis with plasmid pOW350-16.

Plasmid pOW350 serves as useful starting material for constructing other plasmids of the present invention. One such plasmid, designated pOW352, was constructed by ligating the large, ~2.67 kb HindIII restriction fragment of plasmid pOW350 to the ~0.5 kb AsuII-HindIII restriction fragment of plasmid pOW350 and to a synthetic fragment with single-stranded ends, one compatible with the overlap generated by HindIII cleavage and the other with AsuII cleavage. The ~2.67 kb HindIII restriction fragment of plasmid pOW350 encodes the ampicillin resistance-conferring gene and the replicon of plasmid pBR322. The ~0.5 kb AsuII-HindIII restriction fragment of plasmid pOW350 encodes a portion of the nuclease signal peptide and all of staphylococcal nuclease. The synthetic HindIII-AsuII restriction fragment used in the construction of plasmid pOW352 encodes a ribosome-binding site and a portion of a signal peptide of the present invention.

Figure 3:
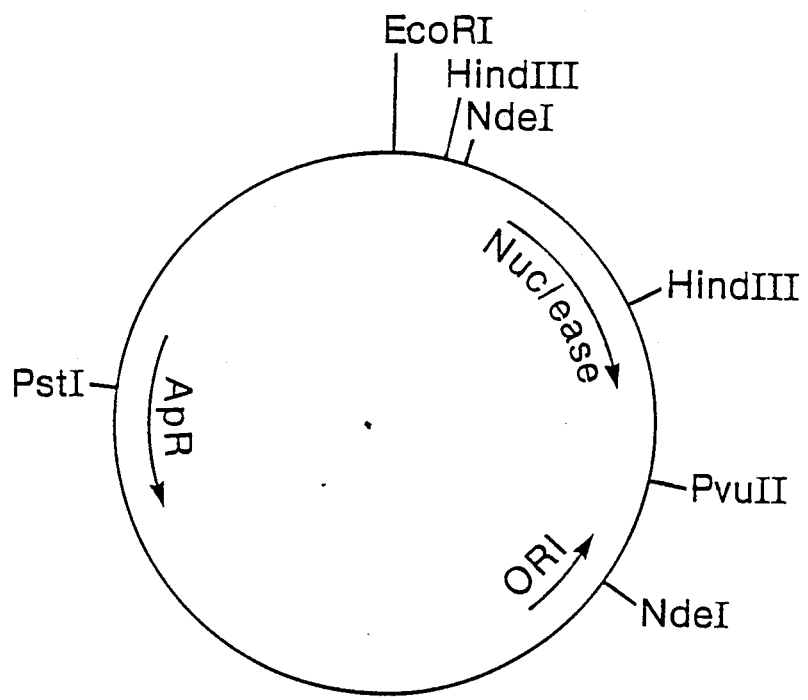
FIG. 3 is a restriction site and function map of plasmid pOW352.

The construction of plasmid pOW352 is described in Example 3, and a restriction site and function map of the plasmid is presented in FIG. 3 of the accompanying drawings. Plasmid pOW352 only differs from plasmid pOW350 in a small portion of the DNA encoding the ribosome-binding site, the initial methionine residue, and a portion of the signal peptide of nuclease. This different DNA sequence, depicted with HindIII and AsuII-compatible single-stranded overlaps is shown below, together with the amino acid sequence encoded by the linker as it resides in plasmid pOW352:

Plasmid pOW352 thus encodes the promoter and a ribosome-binding site of the present invention together with one of the signal peptides of the invention, which differs from that of natural nuclease in that residues 2 (threonine) through 27 (valine) are absent in the signal peptide encoded by plasmid pOW352. Plasmid pOW352 drives expression and secretion of nuclease in E. coli host cells. To construct a Bacillus vector that contains the nuclease gene of plasmid pOW352, plasmid pOW352 was digested with EcoRI and then ligated to the larger EcoRI restriction fragment of plasmid pBC16 to yield plasmid pOW352-16, as described in Example 3.

Plasmids pOW440, pOW350-16, and pOW352-16 each encode a gene that drives expression and secretion of nuclease in Bacillus. A procedure for determining the relative abilities of plasmids pOW440, pOW350-16, and pOW352-16 to drive expression of nuclease in Bacillus host cells is described in Example 4. Nuclease is a useful enzyme. The ease with which nuclease activity can be assayed allows one to use the vectors of the present invention as indicators of mutations that affect a host cell's ability to transcribe DNA, translate mRNA, and secrete protein.

For instance, one can culture Bacillus host cells under conditions that induce mutations in the cellular DNA and then transform the mutated cells with a vector of the present invention. Upon assaying the transformed cell's level of nuclease activity, one thereby determines whether the given mutation increases the cell's ability to produce and/or secrete plasmid-encoded protein.

However, use of the promoter, ribosome-binding site-encoding DNA, and signal peptide-encoding DNA of the present invention is not limited to driving expression of nuclease in Bacillus host cells. Rather, the promoter will drive transcription of any downstream DNA, and the ribosome-binding site-encoding DNA will likewise serve to direct translation, when transcribed into mRNA, of any downstream mRNA.

The promoter and ribosome-binding site-encoding DNA are especially preferred for use in conjunction with either the staphylococcal signal peptide or a signal peptide of the present invention. An important method of the present invention concerns the placement of protein-encoding DNA in relation to DNA encoding the staphylococcal signal peptide or a signal peptide of the present invention to achieve production and secretion of the desired protein. As stated above, nuclease is first synthesized as a 228 amino acid residue protein that is then secreted into the media as a 168 residue protein, the first 60 residues having been deleted during secretion. The present invention teaches that any DNA encoding a protein that is positioned adjacent to and immediately downstream of the signal peptide-encoding DNA of staphylococcal nuclease or of the signal peptide-encoding DNAs of the present invention will encode a useful hybrid gene. Such a gene, when introduced into Bacillus host cells, will drive expression of protein that will be secreted from the cell, and upon secretion, the signal peptide of the protein will be cleaved, leaving only the desired protein.

The NsiI restriction enzyme recognition site present in both the staphylococcal nuclease signal peptide-encoding DNA and the signal peptide-encoding DNAs of the present invention is conveniently positioned for use in constructing recombinant genes that encode such proteins as described above. This NsiI site contains the DNA that encodes the carboxy-terminal alanine of the staphylococcal signal peptide and the signal peptides of the present invention. Due to the nature of NsiI cleavage, no extraneous codons need be introduced in the construction of such a hybrid gene. Thus, any protein desired to be expressed in and secreted from Bacillus can be encoded on a DNA fragment that has an NsiI-compatible overlap at the 5' end of the coding sequence.

The elegance and great utility of this method for constructing hybrid genes to drive expression and secretion of useful proteins is exemplified by an expression vector of the present invention that drives expression and secretion of mature human growth hormone. Plasmid pOW885 contains the promoter, ribosome-binding site-encoding DNA, and shortened signal peptide-encoding DNA of the present invention positioned to drive expression and, upon translation of the mRNA transcribed from the plasmid, secretion of human growth hormone. The transcriptional unit of this novel human growth hormone gene is depicted below:

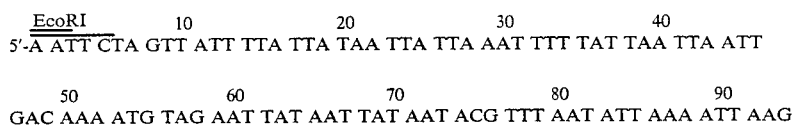

-continued

```
        100              110              120              130             140
CTT AGA AAG GAG GTG ATC TTA TCC ATG GCC ATA TGT ATG GCA ATT GTT
                                    MET ALA ILE CYS MET ALA ILE VAL
                                                 5

150              160              170              180             190
TCA ATA TTA CTT ATA GGG ATG GCT ATC AGT AAT GTT TCG AAA GGG CAA
SER ILE LEU LEU ILE GLY MET ALA ILE SER ASN VAL SER LYS GLY GLN
     10              15                      20

200              210              220             230
TAC GCA AAG AGG TTT TTC TTT TTC GCT ACT AGT TGC TTA GTG TTA ACT
TYR ALA LYS ARG PHE PHE PHE PHE ALA THR SER CYS LEU VAL LEU THR
 25              30                      35                      40

240              250              260              270             280
TTA GTT GTA GTT TCA AGT CTA AGT AGC TCA GCA AAT GCA TTC CCA ACT
LEU VAL VAL VAL SER SER LEU SER SER SER ALA ASN ALA PHE PRO THR
             45                  50                          55
                                                     ↳ first
                                                       residue of HGH 290              300              310              320             330
ATT CCA TTA TCC AGA CTT TTT GAC AAC GCT ATG TTA CGC GCC CAT CGT
ILE PRO LEU SER ARG LEU PHE ASP ASN ALA MET LEU ARG ALA HIS ARG
             60                  65                          70

340              350              360              370             380
CTG CAC CAG CTG GCC TTT GAC ACC TAC CAG GAG TTT GAA GAA GCC TAT
LEU HIS GLN LEU ALA PHE ASP THR TYR GLN GLU PHE GLU GLU ALA TYR
         75                  80                          85

390              400              410              420             430
ATC CCA AAG GAA CAG AAG TAT TCA TTC CTG CAG AAC CCC CAG ACC TCC
ILE PRO LYS GLU GLN LYS TYR SER PHE LEU GLN ASN PRO GLN THR SER
     90                  95                      100

440              450              460              470
CTC TGT TTC TCA GAG TCT ATT CCG ACA CCC TCC AAC AGG GAG GAA ACA
LEU CYS PHE SER GLU SER ILE PRO THR PRO SER ASN ARG GLU GLU THR
105                  110                  115                          120

480              490              500              510             520
CAA CAG AAA TCC AAC CTA GAG CTG CTC CGC ATC TCC CTG CTG CTC ATC
GLN GLN LYS SER ASN LEU GLU LEU LEU ARG ILE SER LEU LEU LEU ILE
                 125                          130                      135

530              540              550              560             570
CAG TCG TGG CTG GAG CCC GTG CAG TTC CTC AGG AGT GTC TTC GCC AAC
GLN SER TRP LEU GLU PRO VAL GLN PHE LEU ARG SER VAL PHE ALA ASN
             140                          145                      150

580              590              600              610             620
AGC CTG GTG TAC GGC GCC TCT GAC AGC AAC GTC TAT GAC CTC CTA AAG
SER LEU VAL TYR GLY ALA SER ASP SER ASN VAL TYR ASP LEU LEU LYS
             155                      160                          165

630              640              650              660             670
GAC CTA GAG GAA GGC ATC CAA ACG CTG ATG GGG AGG CTG GAA GAT GGC
ASP LEU GLU GLU GLY ILE GLN THR LEU MET GLY ARG LEU GLU ASP GLY
170                          175                      180

680              690              700              710
AGC CCC CGG ACT GGG CAG ATC TTC AAG CAG ACC TAC AGC AAG TTC GAC
SER PRO ARG THR GLY GLN ILE PHE LYS GLN THR TYR SER LYS PHE ASP
185                  190                      195                      200

720              730              740              750             760
ACA AAC TCA CAC AAC GAT GAC GCA CTA CTC AAG AAC TAC GGG CTG CTC
THR ASN SER HIS ASN ASP ASP ALA LEU LEU LYS ASN TYR GLY LEU LEU
                 205                      210                      215

770              780              790              800             810
TAC TGC TTC AGG AAG GAC ATG GAC AAG GTC GAG ACA TTC CTG CGC ATC
TYR CYS PHE ARG LYS ASP MET ASP LYS VAL GLU THR PHE LEU ARG ILE
             220                  225                          230

820              830              840              850             860
GTG CAG TGC CGC TCT GTG GAG GGC AGC TGT GGC TTC TAG CTG CCC CCG
VAL GLN CYS ARG SER VAL GLU GLY SER CYS GLY PHE
             235                      240
```

-continued

```
              870          880          890          900          910
       GAT CCA CAG GAC GGG TGT GGT CGC CAT GAT CGC GTA GTC GAT AGT GGC 920          930          940          950
       TCC AAG TAG CGA AGC GAG CAG GAC TGG GCG GCG GCC AAA GCG GTC GGA 960          970          980          990         1000
       CAG TGC TCC GAG AAC GGG TGC GCA TAG AAA TTG CAT CAA CGC ATA TAG 1010         1020         1030         1040         1050
       CGC TAG CAG CAC GCC ATA GTG ACT GGC GAT GCT GTC GGA ATG GAC GAT 1060         1070         1080         1090         1100
       ATC CCG CAA GAG GCC CGG CAG TAC CGG CAT AAC CAA GCC TAT GCC TAC 1110         1120         1130         1140         1150
       AGC ATC CAG GGT GAC GGT GCC GAG GAT GAC GAT GAG CGC ATT GTT AGA 1160         1170         1180         1190
       TTT CAT ACA CGG TGC CTG ACT GCG TTA GCA ATT AAC TGT GAA TAA ACT

HindIII
       1200         1210         1220         1230         1240
       ACC GCA TTA AAG CTT TAG TTC GTC AAG GCT TGG CTA AAG TTG CTT ATG 1250         1260         1270         1280         1290
       TTT ACA AAC CTA ACA ATA CAC ATG AAC AAC ATT TAA GAA AAA GTG AAG 1300         1310         1320         1330         1340
       CAC AAG CGA AAA AAG AGA AAT TAA ATA TTT GGA GCG AAG ACA ACG CTG 1350         1360         1370         1380         1390
       ATT CAG GTC AAT AAT GCT CAT TGT AAA AGT GTC ACT GCT GCT AGT GGC 1400         1410         1420         1430
       ACT TTT ATA ATT TTT AGA TCC CTG CCG TCG TTT ACA ACG TCG TGA C 1440         1450         1460         1470         1480
       TGG GAA AAC CCT GGC GTT ACC CAA CTT AAT CGC CTT GCA GCA CAT CCC PvuII
       1490         1500
       CCT TTC GCC AGC TG-3'
```

Figure 6:
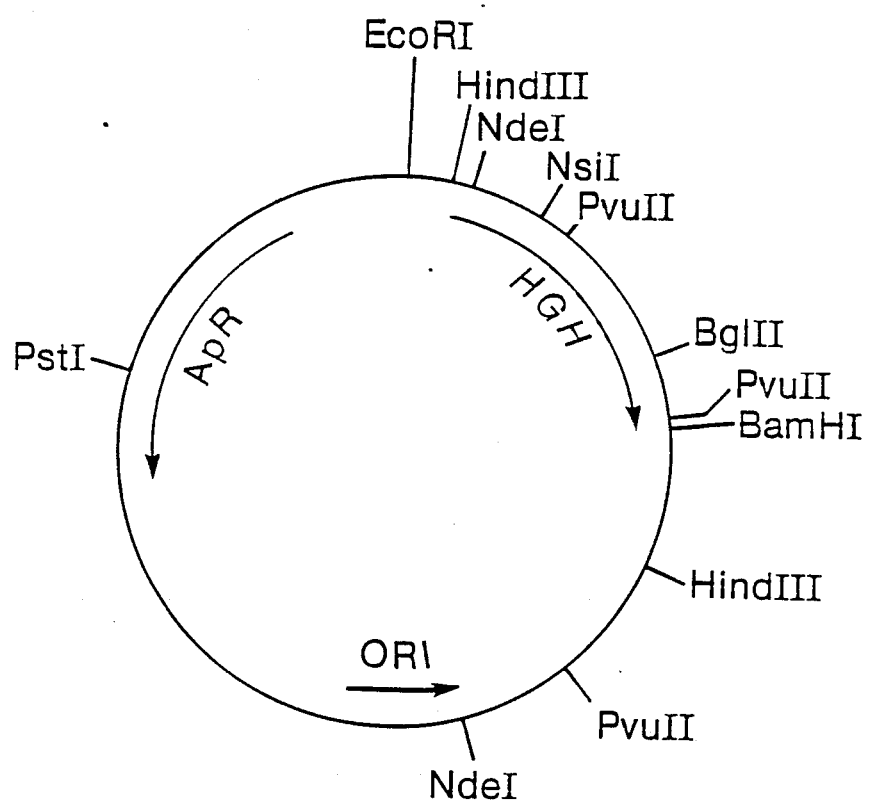
FIG. 6 is a restriction site and function map of plasmid pOW885.

The DNA sequence depicted above begins with an EcoRI restriction enzyme recognition site (although the 5' deoxyguanadyl residue is not depicted) and ends with a PvuII restriction enzyme recognition site. sequence from the HindIII site to the PvuII site in the 3'-noncoding region of the above-depicted sequence encodes the transcription termination signal of a Bacillus gene. Plasmid pOW885 can be constructed by inserting the above-depicted fragment, synthesized as an EcoRI-PvuII restriction fragment with single-stranded DNA overlaps characteristic of EcoRI and PvuII cleavage, into EcoRI-PvuII-digested plasmid pBR322. A restriction site and function map of plasmid pOW885 is presented in FIG. 6 of the accompanying drawings.

Plasmid pOW885 also drives expression and secretion of human growth hormone in E. coli host cells. The human growth hormone (HGH) collected from the media of cells containing plasmid pOW885 contains the residues number 54 to 244, above. The promoter, ribosome-binding site-encoding DNA, and signal peptide-encoding DNA of the present invention function quite well in E. coli . Thus, although Bacillus is the preferred host for use with the promoter, ribosome-binding site-encoding DNA, and signal peptide-encoding DNA compounds of the present invention, these vectors and compounds are also quite useful in E. coli. Plasmid pOW885 can be readily modified to function in Bacillus host cells by inserting the larger EcoRI restriction fragment of plasmid pBC16 into the single EcoRI site of plasmid pOW885 and recircularizing to form plasmid pOW885-16.

Although E. coli/pOW885 transformants produced high levels of human growth hormone, when plasmid pOW885-16 was first transformed into Bacillus host cells, the expression levels were much lower. Thus, whereas plasmid pOW350-16 of the present invention drives expression of nuclease in Bacillus host cells to levels of about 500 µg/ml, the levels of expression of another protein from a plasmid identical to pOW350-16 in all but the nuclease-encoding sequences may be lower than optimum. In fact, the present state of the art of genetic engineering does not allow for the accurate prediction or selection of particular transformants that express products at optimum levels from among the population of transformants that are constructed.

The present invention provides a solution to this problem by affording a method for identifying host cells with increased ability to express a heterologous gene product, such method comprising: (1) transforming the host cell with a recombinant DNA vector that comprises a gene that drives production of an mRNA transcript that encodes a ribosome-binding site, a heterologous gene product, and nuclease activity; (2) selecting those transformants that produce higher than the average level of nuclease activity as determined by visual or biochemical assay; and (3) selecting from the transformants of step 2, transformants that exhibit increased nuclease activity due to a genomic change rather than a change in the plasmid DNA. This latter selection can be easily done by curing the transformants obtained in step (2) of vector DNA, then retransforming with the vector used in step (1), and finally determining if nuclease levels still remain higher than average, indicating a genomic, rather than plasmidic, change. This process will enable identification of cells with an increased ability to synthesize and secrete the heterologous gene product.

Thus, if initial expression levels of a heterologous gene product are low in a given host cell, such as Bacillus, expression levels can be increased by inserting the coding sequence for nuclease activity into the expression vector so that the heterologous protein-encoding mRNA transcript produced from the vector also encodes nuclease. The nuclease-encoding sequences may be placed either upstream or downstream of the heterologous protein encoding sequence so that the mRNA transcript produced from the vector encodes either (1) a ribosome-binding site followed by the coding sequence for a single, fusion protein that contains the heterologous protein fused to a protein with nuclease activity; or (2) a ribosome-binding site followed by the coding sequences for two proteins, the heterologous protein and a protein with nuclease activity, which are separated by another ribosome-binding site followed by the start codon of the second coding sequence.

Once such a nuclease/heterologous protein-encoding vector is constructed, the vector can be transformed into the appropriate recipient host cell. The transformed cells are subjected to mutagenesis, and the mutated cells are assayed for higher than average levels of nuclease than unmutated cells. Mutated cells that express higher levels of nuclease activity are then transformed with vectors encoding the heterologous protein alone. As demonstrated in Example 5, such mutants produce more heterologous protein.

The method described above has been exemplified using plasmid pOW360, which contains a gene that encodes a human growth hormone-nuclease fusion protein and is depicted below:

```
    EcoRI         10              20              30              40
5'-A ATT CTA GTT ATT TTA TTA TAA TTA TTA AAT TTT TAT TAA TTA ATT 50              60              70              80              90
   GAC AAA ATG TAG AAT TAT AAT TAT AAT ACG TTT AAT ATT AAA ATT AAG 100             110             120             130             140
   CTT AGA AAG GAG GTG ATC TTA TCC ATG GCC ATA TGT ATG GCA ATT GTT
                                       MET ALA ILE CYS MET ALA ILE VAL
                                                                     5

150             160             170             180             190
   TCA ATA TTA CTT ATA GGG ATG GCT ATC AGT AAT GTT TCG AAA GGG CAA
   SER ILE LEU LEU ILE GLY MET ALA ILE SER ASN VAL SER LYS GLY GLN
    10                       15                  20

200             210             220             230
   TAC GCA AAG AGG TTT TTC TTT TTC GCT ACT AGT TGC TTA GTG TTA ACT
   TYR ALA LYS ARG PHE PHE PHE PHE ALA THR SER CYS LEU VAL LEU THR
    25              30                      35                      40

240         250             260             270             280
   TTA GTT GTA GTT TCA AGT CTA AGT AGC TCA GCA AAT GCA TTC CCA ACT
   LEU VAL VAL VAL SER SER LEU SER SER SER ALA ASN ALA PHE PRO THR
                    45                      50                   55
                                                                 └─> first
                                                                 residue of HGH 290             300             310             320             330
   ATT CCA TTA TCC AGA CTT TTT GAC AAC GCT ATG TTA CGC GCC CAT CGT
   ILE PRO LEU SER ARG LEU PHE ASP ASN ALA MET LEU ARG ALA HIS ARG
                60                      65                      70

340             350             360             370             380
   CTG CAC CAG CTG GCC TTT GAC ACC TAC CAG GAG TTT GAA GAA GCC TAT
   LEU HIS GLN LEU ALA PHE ASP THR TYR GLN GLU PHE GLU GLU ALA TYR
    75                      80                      85

390             400             410             420             430
   ATC CCA AAG GAA CAG AAG TAT TCA TTC CTG CAG AAC CCC CAG ACC TCC
   ILE PRO LYS GLU GLN LYS TYR SER PHE LEU GLN ASN PRO GLN THR SER
    90                      95                      100

440             450             460             470
   CTC TGT TTC TCA GAG TCT ATT CCG ACA CCC TCC AAC AGG GAG GAA ACA
   LEU CYS PHE SER GLU SER ILE PRO THR PRO SER ASN ARG GLU GLU THR
    105                     110                     115                 120

480             490             500             510             520
   CAA CAG AAA TCC AAC CTA GAG CTG CTC CGC ATC TCC CTG CTG CTC ATC
   GLN GLN LYS SER ASN LEU GLU LEU LEU ARG ILE SER LEU LEU LEU ILE
                        125                     130                     135
```

```
      530             540             550            560              570
CAG TCG TGG CTG GAG CCC GTG CAG TTC CTC AGG AGT GTC TTC GCC AAC
GLN SER TRP LEU GLU PRO VAL GLN PHE LEU ARG SER VAL PHE ALA ASN
           140                         145                150

580             590            600             610            620
AGC CTG GTG TAC GGC GCC TCT GAC AGC AAC GTC TAT GAC CTC CTA AAG
SER LEU VAL TYR GLY ALA SER ASP SER ASN VAL TYR ASP LEU LEU LYS
        155                        160                 165

630             640             650            660             670
GAC CTA GAG GAA GGC ATC CAA ACG CTG ATG GGG AGG CTG GAA GAT GGC
ASP LEU GLU GLU GLY ILE GLN THR LEU MET GLY ARG LEU GLU ASP GLY
             170                     175                    180

680             690             700            710
AGC CCC CGG ACT GGG CAG ATC TTC AAG CAG ACC TAC AGC AAG TTC GAC
SER PRO ARG THR GLY GLN ILE PHE LYS GLN THR TYR SER LYS PHE ASP
185                    190                     195                   200

720             730            740            750            760
ACA AAC TCA CAC AAC GAT GAC GCA CTA CTC AAG AAC TAC GGG CTG CTC
THR ASN SER HIS ASN ASP ASP ALA LEU LEU LYS ASN TYR GLY LEU LEU
                  205                      210                 215

770             780            790           800             810
TAC TGC TTC AGG AAG GAC ATG GAC AAG GTC GAG ACA TTC CTG CGC ATC
TYR CYS PHE ARG LYS ASP MET ASP LYS VAL GLU THR PHE LEU ARG ILE
              220                    225                    230

820             830             840            850             860
GTG CAG TGC CGC TCT GTG GAG GGC AGC ATG GAT CCA ACA GTA TAT AGT
VAL GLN CYS ARG SER VAL GLU GLY SER MET ASP PRO THR VAL TYR SER
           235                     240                   245
             last residue derived from HGH ←┘         ↓
                                              beginning of nuclease residues 870             880            890             900             910
GCA ACT TCA ACT AAA AAA TTA CAT AAA GAA CCT GCG ACT TTA ATT AAA
ALA THR SER THR LYS LYS LEU HIS LYS GLU PRO ALA THR LEU ILE LYS
                              255                    260
   ↳ first residue of nuclease A 920             930            940            950
GCG ATT GAT GGT GAT ACG GTT AAA TTA ATG TAC AAA GGT CAA CCA ATG
ALA ILE ASP GLY ASP THR VAL LYS LEU MET TYR LYS GLY GLN PRO MET
265                   270                    275                   280

960            970            980            990           1000
ACA TTC AGA CTA TTA TTG GTT GAT ACA CCT GAA ACA AAG CAT CCT AAA
THR PHE ARG LEU LEU LEU VAL ASP THR PRO GLU THR LYS HIS PRO LYS
              285                      290                  295

1010            1020            1030            1040            1050
AAA GGT GTA GAG AAA TAT GGT CCT GAA GCA AGT GCA TTT ACG AAA AAA
LYS GLY VAL GLU LYS TYR GLY PRO GLU ALA SER ALA PHE THR LYS LYS
           300                     305                     310

1060            1070           1080            1090            1100
ATG GTA GAA AAT GCA AAG AAA ATT GAA GTC GAG TTT GAC AAA GGT CAA
MET VAL GLU ASN ALA LYS LYS ILE GLU VAL GLU PHE ASP LYS GLY GLN
      315                     320                    325

1110            1120            1130           1140            1150
AGA ACT GAT AAA TAT GGA CGT GGC TTA GCG TAT ATT TAT GCT GAT GGA
ARG THR ASP LYS TYR GLY ARG GLY LEU ALA TYR ILE TYR ALA ASP GLY
       330                     335                    340

1160           1170            1180            1190
AAA ATG GTA AAC GAA GCT TTA GTT CGT CAA GGC TTG GCT AAA GTT GCT
LYS MET VAL ASN GLU ALA LEU VAL ARG GLN GLY LEU ALA LYS VAL ALA
345                     350                    355                   360

1200            1210            1220            1230            1240
TAT GTT TAC AAA CCT AAC AAT ACA CAT GAA CAA CAT TTA AGA AAA AGT
TYR VAL TYR LYS PRO ASN ASN THR HIS GLU GLN HIS LEU ARG LYS SER
                365                     370                    375
```

-continued

```
        1250            1260            1270            1280            1290
GAA GCA CAA GCG AAA AAA GAG AAA TTA AAT ATT TGG AGC GAA GAC AAC
GLU ALA GLN ALA LYS LYS GLU LYS LEU ASN ILE TRP SER GLU ASP ASN
        380                             385                     390

1300            1310            1320            1330            1340
GCT GAT TCA GGT CAA TAA TGC TCA TTG TAA AAG TGT CAC TGC TGC TAG
ALA ASP SER GLY GLN
        395

1350            1360            1370            1380            1390
TGG CAC TTT TAT AAT TTT TAG ATC CCT GGC CGT CGT TTT ACA ACG TCG 1400            1410            1420            1430
TGA CTG GGA AAA CCC TGG CGT TAC CCA ACT TAA TCG CCT TGC AGC ACA

PvuII
1440            1450
TCC CCC TTT CGC CAG CTG-3'
```

Figure 4:
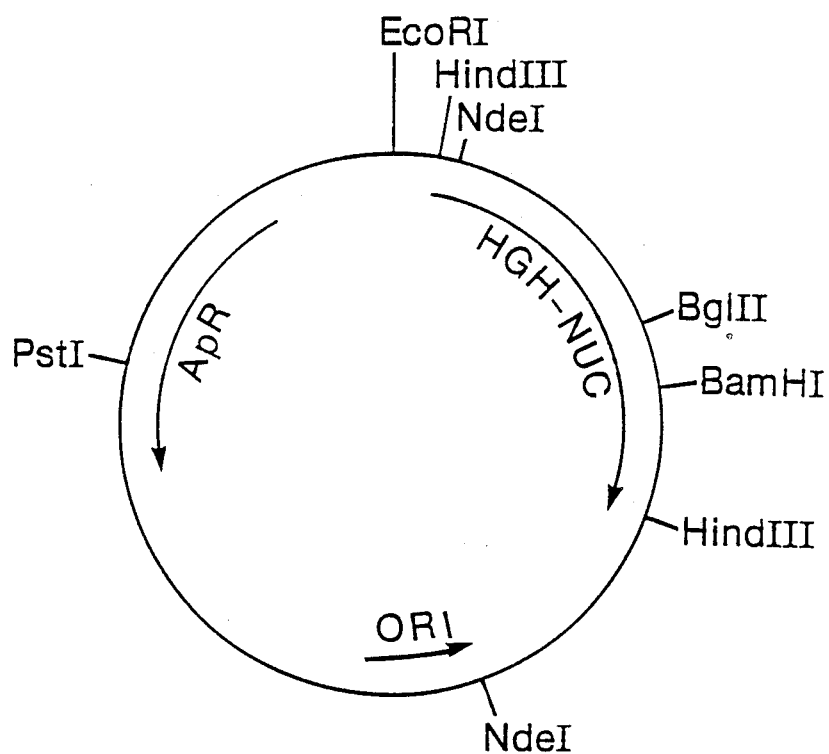
FIG. 4 is a restriction site and function map of plasmid pOW360.

Plasmid pOW360 can be constructed by inserting the above-depicted DNA segment, as an EcoRI-PvuII restriction fragment, into EcoRI-PvuII-digested plasmid pBR322, thus replacing the ~2.07 kb EcoRI-PvuII restriction fragment of plasmid pBR322 that contains the tetracycline resistance-conferring gene. Plasmid pOW360 drives expression and secretion of a human growth hormone-nuclease fusion protein in *E. coli* host cells; the first 53 amino-terminal residues of the protein, a signal peptide of the present invention, are removed from the protein during secretion. In addition, the fusion protein produced in *E. coli* and Bacillus transformants containing plasmid pOW360 is cleaved to yield nuclease A and a human growth hormone derivative in which the three carboxy-terminal residues CYS-GLY-PHE are replaced by the 8-residue peptide MET-ASP-PRO-THR-VAL-TYR-SER-ALA. Plasmid pOW360 is readily modified to yield a Bacillus expression vector by inserting the larger EcoRI restriction fragment of plasmid pBC16 into the single EcoRI site of plasmid pOW360, producing plasmid pOW360-16. A restriction site and function map of plasmid pOW360 is presented in FIG. 4 of the accompanying drawings.

Plasmid pOW360-16 was transformed into Bacillus subtilis host cells, and the transformed cells were subjected to mutagenesis, as described in Example 5. The mutants that expressed higher levels of nuclease were cured of plasmid pOW360-16 and then used as hosts for plasmid pOW885-16. Significantly higher levels of human growth hormone were secreted from the mutated cells containing plasmid pOW885-16 than from unmutated *Bacillus subtilis*/pOW885 transformants.

Although plasmids pOW360 and pOW360-16 utilize the novel promoter, ribosome-binding site-encoding DNA, and signal peptide-encoding DNA of the present invention to exemplify the method of obtaining mutants with increased ability to express heterologous gene products, the method is not limited to a particular set of regulatory sequences, or to a particular heterologous gene, or even to a particular host cell. The method can be used in host cells other than Bacillus, such as *E. coli*, so long as the regulatory sequences responsible for driving transcription of the heterologous gene function in the host cell. Plasmid pOW362 contains a gene that utilizes the Bacillus veg promoter, a synthetic ribosome-binding site-encoding DNA, and a synthetic signal peptide-encoding DNA similar to that of the α-amylase gene of *Bacillus amyloliquefaciens* to drive expression of a fusion protein containing proinsulin and nuclease. The Bacillus veg promoter can be isolated from plasmid pMS480, deposited in *E. coli* K12 JA221/pMS480 (NRRL B-15258), and used to construct the promoter and signal peptide-encoding DNA in plasmid pOW362 as described in U.S. Pat. No. 4,559,300. Plasmid pOW362 is therefore useful in the method to obtain Bacillus mutants with an increased ability, over wild-type cells, to produce and secrete proinsulin.

The proinsulin-nuclease gene contained on plasmid pOW362 is depicted below.

```
EcoRI
5'-GAATTC -- about 340 nucleotides of DNA sequence upstream
of the Bacillus veg promotor --

10              20              30              40
          G TCA AAA TAA TTT TAT TGA CAA CGT CTT ATT AAC GTT AGT ATA ATT 50              60              70              80              90
      TAA ATT TTA TTT GAC AAA AAT GGG CTC GTG TTG TAC AAT AAA TGT AGT 100             110             120             130             140
      GAG GTG GAT GCC ATG GTT CAA AAA CGA AAG CGG ACA GTT TCG TTC AGA
                          MET VAL GLN LYS ARG LYS ARG THR VAL SER PHE ARG
                              5                   10

150             160             170             180             190
      CTT GTG CTT ATG TGC ACG CTG TTA TTT GTC AGT TTG CCG ATT ACA AAA
      LEU VAL LEU MET CYS THR LEU LEU PHE VAL SER LEU PRO ILE THR LYS
              15                  20                  25
```

-continued

```
          200           210           220           230
ACA TCA GCC ATG GAT CCA ACA GTA TAT AGT GCA ACT TTC GTT AAC CAA
THR SER ALA MET ASP PRO THR VAL TYR SER ALA THR PHE VAL ASN GLN
         30   ↓              35                  40   ┐
first residue of                                      └→first residue
secreted fusion protein                                 of proinsulin 240           250           260           270           280
CAC TTG TGT GGT TCT CAC CTC GTT GAA GCT CTC TAC CTA GTG TGC GGG
HIS LEU CYS GLY SER HIS LEU VAL GLU ALA LEU TYR LEU VAL CYS GLY
45                  50                  55                  60

290           300           310           320           330
GAA CGA GGC TTC TTC TAC ACA CCC AAG ACC CGC CGG GAG GCA GAG GAC
GLU ARG GLY PHE PHE TYR THR PRO LYS THR ARG ARG GLU ALA GLU ASP
              65                  70                  75

340           350           360           370           380
CTG CAG GTG GGG CAG GTG GAG CTG GGC GGG GGC CCT GGT GCA GGC AGC
LEU GLN VAL GLY GLN VAL GLU LEU GLY GLY GLY PRO GLY ALA GLY SER
         80                  85                  90

390           400           410           420           430
CTG CAG CCC TTG GCC CTG GAG GGG TCC CTG CAG AAG CGT GGC ATT GTG
LEU GLN PRO LEU ALA LEU GLU GLY SER LEU GLN LYS ARG GLY ILE VAL
         95                  100                 105

440           450           460           470
GAA CAA TGC TGT ACC AGC ATC TGC TCC CTC TAC CAG GAT CCA ACA GTA
GLU GLN CYS CYS THR SER ILE CYS SER LEU TYR GLN ASP PRO THR VAL
     110                 115                    ┐    ┐
                    last proinsulin-derived residue ←┘    └→first nuclease-
                                                             derived residue 480           490           500           510           520
TAT AGT GCA ACT TCA ACT AAA AAA TTA CAT AAA GAA CCT GCG ACT TTA
TYR SER ALA THR SER THR LYS LYS LEU HIS LYS GLU PRO ALA THR LEU
125      ┐          130                 135                 140
         └→first residue of nuclease A 530           540           550           560           570
ATT AAA GCG ATT GAT GGT GAT ACG GTT AAA TTA ATG TAC AAA GGT CAA
ILE LYS ALA ILE ASP GLY ASP THR VAL LYS LEU MET TYR LYS GLY GLN
              145                 150                 155

580           590           600           610           620
CCA ATG ACA TTC AGA CTA TTA TTG GTT GAT ACA CCT GAA ACA AAG CAT
PRO MET THR PHE ARG LEU LEU LEU VAL ASP THR PRO GLU THR LYS HIS
         160                 165                 170

630           640           650           660           670
CCT AAA AAA GGT GTA GAG AAA TAT GGT CCT GAA GCA AGT GCA TTT ACG
PRO LYS LYS GLY VAL GLU LYS TYR GLY PRO GLU ALA SER ALA PHE THR
         175                 180                 185

680           690           700           710
AAA AAA ATG GTA GAA AAT GCA AAG AAA ATT GAA GTC GAG TTT GAC AAA
LYS LYS MET VAL GLU ASN ALA LYS LYS ILE GLU VAL GLU PHE ASP LYS
         190                 195                 200

720           730           740           750           760
GGT CAA AGA ACT GAT AAA TAT GGA CGT GGC TTA GCG TAT ATT TAT GCT
GLY GLN ARG THR ASP LYS TYR GLY ARG GLY LEU ALA TYR ILE TYR ALA
205                 210                 215                 220

770           780           790           800           810
GAT GGA AAA ATG GTA AAC GAA GCT TTA GTT CGT CAA GGC TTG GCT AAA
ASP GLY LYS MET VAL ASN GLU ALA LEU VAL ARG GLN GLY LEU ALA LYS
              225                 230                 235

820           830           840           850           860
GTT GCT TAT GTT TAC AAA CCT AAC AAT ACA CAT GAA CAA CAT TTA AGA
VAL ALA TYR VAL TYR LYS PRO ASN ASN THR HIS GLU GLN HIS LEU ARG
         240                 245                 250

870           880           890           900           910
AAA AGT GAA GCA CAA GCG AAA AAA GAG AAA TTA AAT ATT TGG AGC GAA
LYS SER GLU ALA GLN ALA LYS LYS GLU LYS LEU ASN ILE TRP SER GLU
         255                 260                 265
```

```
                    920         930         940         950
           GAC AAC GCT GAT TCA GGT CAA TAA TGC TCA TTG TAA AAG TGT CAC TGC
           ASP ASN ALA ASP SER GLY GLN
            270                 275

960         970         980         990         1000
           TGC TAG TGG CAC TTT TAT AAT TTT TAG ATC CCT GGC CGT CGT TTT ACA 1010        1020        1030        1040        1050
           ACG TCG TGA CTG GGA AAA CCC TGG CGT TAC CCA ACT TAA TCG CCT TGC

PvuII
             1060        1070          ‾‾‾‾‾‾‾
           AGC ACA TCC CCC TTT CGC CAG CTG-3'
```

Figure 5:
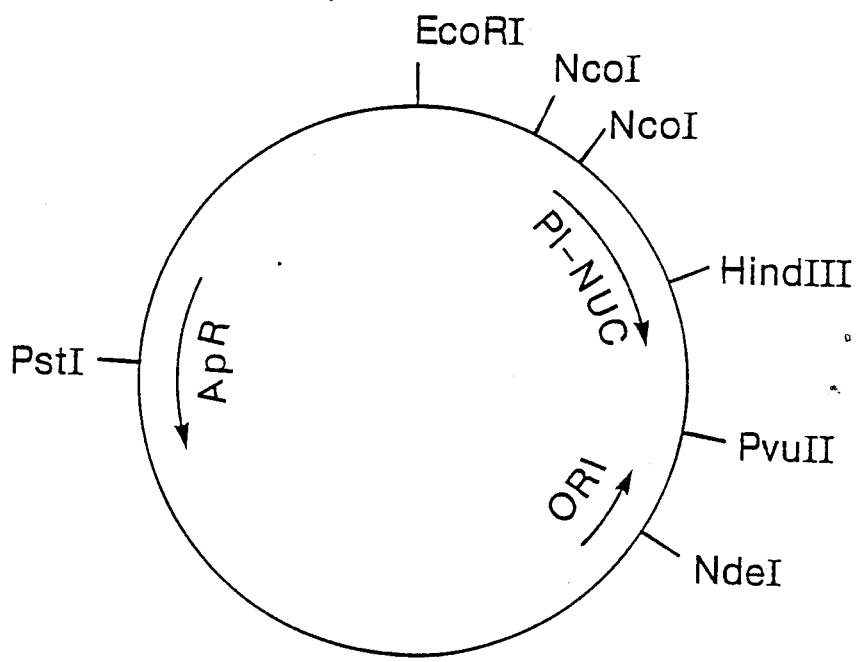
FIG. 5 is a restriction site and function map of plasmid pOW362.

Plasmid pOW362 drives expression and secretion of a proinsulin-nuclease fusion protein in *E. coli* host cells. This fusion protein is first synthesized as a 275-residue protein, of which the first 31 amino-terminal residues, the α-amylase-type signal peptide, are removed during secretion of the fusion protein. The fusion protein undergoes further cleavage, which results in the production of two proteins: (1) a proinsulin-like protein that contains residues 32 to 127; and (2) nuclease A protein. The proinsulin-like protein differs from proinsulin in both the amino- and carboxy-terminal portions of the protein. The first nine amino-terminal residues of the secreted fusion protein (residues 32-40) are not found in natural proinsulin, and in the region of the fusion protein corresponding to the carboxy terminus of proinsulin, the secreted fusion protein contains GLN-ASP-PRO-THR-VAL-TYR-SER-ALA (residues 120 through 127), whereas proinsulin contains GLN-LEU-ASP-ASN-TYR-CYS-ASN. Plasmid pOW362 can be constructed by inserting the above-depicted DNA sequence, as an EcoRI-PvuII restriction fragment, into EcoRI-PvuII-digested plasmid pBR322. A restriction site and function map of plasmid pOW362 is presented in FIG. 5 of the accompanying drawings. A Bacillus-functional derivative of plasmid pOW362, designated pOW362-16, was constructed by inserting the larger EcoRI restriction fragment of plasmid pBC16 into the single EcoRI site of plasmid pOW362. Plasmid pOW362-16 drives expression and secretion of the proinsulin-nuclease fusion protein in Bacillus host cells to produce the same proteins plasmid pOW362 produces in *E. coli*. Plasmid pOW362-16 can thus be used in accordance with the method of the present invention to identify Bacillus mutants with increased ability to synthesize and secrete proinsulin.

The present invention is particularly versatile and can be applied to the production of any functional polypeptide encoded in a recombinant DNA expression vector. A preferred recombinant DNA expression vector is the plasmid, although bacteriophage and other useful vectors will be apparent to those skilled in the art. In addition, various sequences that code for functional polypeptides can be substituted for the illustrative staphylococcal nuclease, human growth hormone, and proinsulin coding sequences specifically exemplified. Such sequences include those that are naturally occurring, non-naturally occurring, and in part naturally occurring and in part synthetic or non-naturally occurring. More particularly, illustrative sequences can code for human insulin A-chain, human insulin B-chain, non-human insulin A-chain, non-human insulin B-chain, non-human growth hormone, bovine growth hormone, porcine growth hormone, human interferon, non-human interferon, viral antigen, urokinase, human tissue plasminogen activator, interleukin I, interleukin II, growth hormone releasing factor, any hormone, any enzyme, and virtually any other polypeptide with research or commercial value.

The recombinant DNA expression vectors and method of the present invention are not limited for use in a single species or strain. To the contrary, the vectors and method are broadly applicable and can be employed using host cells of many taxa, particularly the restrictionless strains of Bacillus, Staphylococcus, and *E. coli*. Restrictionless strains are readily selected and isolated from Bacillus and other taxa by conventional procedures and extensions of principles well known in the art (Lomovskaya et al., 1980, Microbiological Reviews 44:206). Host cells of restrictionless strains lack restriction enzymes and therefore do not cut or degrade plasmid DNA upon transformation. For purposes of the present application, host cells containing restriction enzymes that do not cut any of the restriction sites of the present vectors are also considered restrictionless.

Preferred host cells of restrictionless strains of Bacillus in which the present method and vectors are especially useful include restrictionless cells of, for example, *B. subtilis, B. subtilis* MI112, *B. subtilis* SR22, *B. thuringiensis, B. thuringiensis* var. *israeliensis, B. cereus, B. anthracis, B. piliformis, B. tropicus, B. alvei, B. megaterium, B. pumilus, B. licheniformis, B. polymyxa, B. macerans, B. circulans, B. stearothermophilus, B. coaqulans, B. firmus, B. brevis, B. sphaericus, B. pasteurii, B. fastidiosus, B. larvae, B. lentimorbus, B. apiarus, B. brevis, B. amyloliquifaciens, B. laterosporus,* and *B. popillae*.

Preferred host cells of restrictionless strains of Staphylococcus taxa in which the present method and vectors are useful include restrictionless cells of, for example, *S. aureus, S. carnosus, S. epidermidis,* and *S. saprophyticus*. The invention is not limited for use in Bacillus and Staohylococcus but can also be used in various *E. coli* host cells. Preferred *E. coli* host cells include, but are not limited to, *E. coli* K12, *E. coli* K12 JA221, *E. coli* K12 HB101, *E. coli* K12 C600, E. coli K12 C600$m_k^-R_k^-$, *E. coli* K12 C600$M_k^+R_k^-$, and *E. coli* K12 RV308.

While all the embodiments of the present invention are useful, some of the present expression vectors are preferred. Accordingly, preferred vectors are plasmids pOW350, pOW352, pOW885, pOW350-16, pOW352-16, and pOW885-16, and preferred transformants are *E. coli* K12/pOW350, *E. coli* K12/pOW352, *E. coli* K12/pOW885, *Bacillus subtilis* MI112/pOW350-16, *B. subtilis* MI112/pOW352-16, *B. subtilis* MI112/pOW885-16, *B. subtilis* SR22/pOW350-16 and *B. subtilis* SR22/pOW352-16, and *B. subtilis* SR22/pOW885-16.

The recombinant DNA expression vectors and transformants of the present invention have broad utility and help fill the need for expression vehicles, especially for use in Bacillus. The present invention thus allows for the genetic expression and secretion in Bacillus of an assortment of important products including those now bioproduced in *E. coli*. This is especially advantageous because large scale fermentation of Bacillus is better known and understood than is fermentation of *E. coli*. In fact, commercial fermentation of *E. coli* is still highly experimental and fraught with difficulty. The present invention circumvents this problem by providing the alternative of producing compounds (some of which are now biosynthesized in *E. coli*) such as, for example, human insulin A-chain, human insulin B-chain, human proinsulin and growth hormone and the like in Bacillus. This can be done because the present vectors are highly versatile and can accommodate DNA sequences that encode virtually any functional polypeptide. Thus, the present invention allows for flexibility in the choice of hosts and provides a means for using Bacillus in the bioproduction and secretion of polypeptides and other gene products.

The ability of the present transformants to secrete polypeptide products is commercially advantageous. For example, isolation and purification of polypeptides can be done continuously during fermentation without requiring lytic destruction of the host cells to isolate product. Secretion also affords protection against proteolytic degradation of gene products by naturally occurring intracellular protease enzymes. Microorganisms are notorious for producing enzymes that digest foreign polypeptides. The present method for identifying mutants with increased ability to synthesize a foreign polypeptide provides a means for overcoming the effects of these degradative enzymes above and beyond the role played by secretion, which also helps circumvent this degradation. Secretion provides a means for removing susceptible polypeptides from the host cell before proteolytic degradation can occur. In addition, host cells are also protected from the toxic effects of a given gene product, because secretion prevents the deleterious effects and possible cell death associated with intracellular build-up of the gene product.

*Bacillus subtilis* MI112/pOW350-16, *B. subtilis* MI112/pOW352-16, and *E. coli* K12 JA221/pOW350, as respective sources of plasmids pOW350-16, pOW352-16 and pOW350, can be cultured in a number of ways using any of several different media. Carbohydrate sources preferred for use in a culture medium include, for example, molasses, glucose, dextrin, and glycerol, and nitrogen sources include, for example, soy flour, amino acid mixtures, and peptones. Nutrient inorganic salts are also incorporated into the media and include the customary salts capable of yielding sodium, potassium, ammonium, calcium, phosphate, chloride, sulfate, and like ions. As is necessary for the growth and development of other microorganisms, essential trace elements are also added to the media. Such trace elements are commonly supplied as impurities incidental to the addition of other constituents of the medium.

*Bacillus subtilis* MI112/pOW350-16, *B. subtilis* MI112/pOW352-16, and *B. subtilis* MI112/pOW885-16 are grown under aerobic culture conditions over a relatively wide pH range of about 5 to 8.5 at temperatures ranging from about 25° to 45° C. For production of plasmid-encoded gene products, however, it is desirable to start with a culture medium at a pH of about 7 and maintain a culture temperature of about 30° C. Culturing *Bacillus subtilis* MI112/pOW350-16, *B. subtilis* MI112/352-16, and *B. subtilis* MI112/pOW885-16 under the aforementioned conditions results in a reservoir of cells and media from which the aforementioned plasmid-encoded products are isolated conveniently by techniques well known in the art.

*E. coli* K12/pOW350, *E. coli* K12/pOW352, and *E. coli* K12/pOW885 are grown under aerobic culture conditions over a relatively wide pH range of about 6.5 to 8 at temperatures ranging from about 25° to 40° C. It is desirable to start with a culture medium at a pH of about 7.2 and maintain a culture temperature of about 37° C. Culturing the *E. coli* cells, under the aforementioned conditions, results in a reservoir of cells from which the plasmids and plasmid-encoded products are isolated by techniques well known in the art.

The following examples further illustrate and detail, but in no way limit the scope of, the invention disclosed herein. Both an explanation of and the actual procedures for constructing the invention are described where appropriate.

EXAMPLE 1

Culture of *Bacillus subtilis* MI112/pOW440

Figure 1:
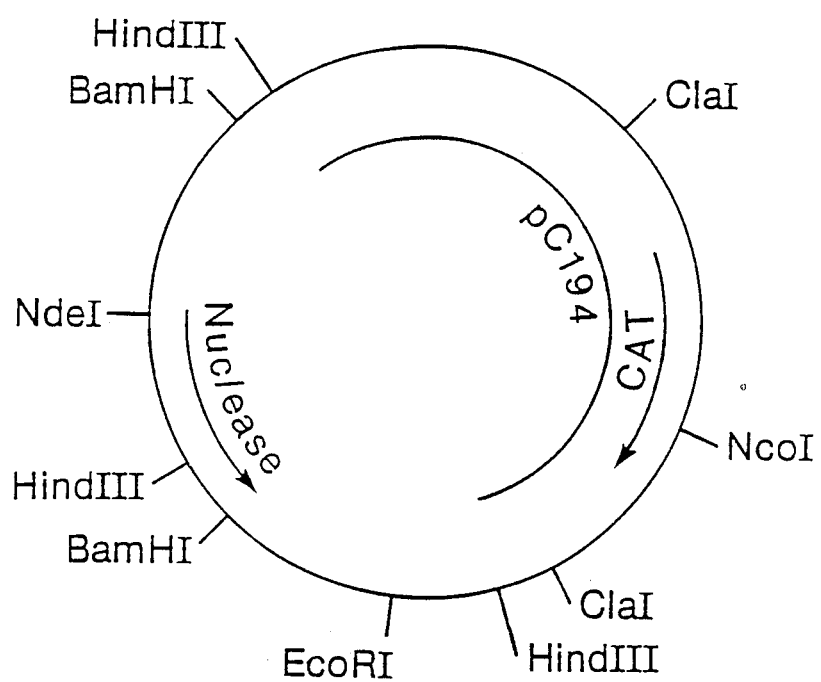
FIG. 1 is a restriction site and function map of plasmid pOW440.

A vegetative culture of *Bacillus subtilis* MI112/pOW440 (NRRL B-15887) was conventionally prepared by inoculating sterile PenAssay broth (Difco, Detroit, Mich.) containing 20 µg/m of chloramphenicol with the above-specified strain and growing the resultant starter culture at 30° C. with vigorous aeration for about 16 hours. About 2–5% of the volume of the starter culture is then added to fresh, sterile PenAssay broth and grown at 30° C until the culture is turbid (about 150–200 Klett units on a Klett-Summerson Colorimeter (Klett Mfg. Co., Inc. New York, N.Y., with filter #60). The cell media was assayed for nuclease activity as described in Example 4. A restriction site and function map of plasmid pOW440 is presented in FIG. 1 of the accompanying drawings.

EXAMPLE 2

Construction of *Bacillus subtilis* MI112/pOW350-16

A. Isolation of Plasmid pOW350

The bacterium *E. coli* K12 JA221/pOW350 (NRRL B-18119) was cultured in ~5 ml of TY broth (10 g Bacto-Tryptone (Difco), 5 g Bacto-Yeast extract, and 5 g NaCl, per liter) with 100 µg/ml of antibiotic ampicillin a 37° C., with aeration. After about 18 hours incubation, about 1.0 ml of the culture was transferred to a 1.5 ml Eppendorf tube and centrifuged for about 15 seconds. Unless otherwise indicated, all manipulations were done at ambient temperature. The resultant supernatant was removed with a fine-tip aspirator and the cell pellet suspended in about 100 µl of freshly prepared lysozyme solution that contained 2 mg/ml lysozyme, 50 mM glucose, 10 mM EDTA (ethylene diaminetetraacetate) and 25 mM Tris-HCl, pH=8. After incubation at 0° C. for 30 minutes, about 200 µl SDS (sodium dodecyl sulfate) solution (0.2 N NaOH and 1% SDS) were added to the cell mixture, and then, the tube was gently vortexed and maintained at 0° C. for 5 minutes. Next, about 150 µl of 3 M sodium acetate (NaOAc) (prepared by dissolving 3 moles of sodium acetate in a minimum of water, adjusting the pH to 4.8 with glacial acetic acid, and then adjusting the volume to 1 L) were added to the solution of lysed cells.

The tube containing the solution of lysed cells was maintained at 0° C. for 60 minutes and then centrifuged for 5 minutes to yield an almost clear supernatant. About 0.4 ml of the supernatant was transferred to a second centrifuge tube to which 1 ml of cold ethanol was added. After the tube was held at −20° C. for 30 minutes, the resultant precipitate was collected by centrifugation and the supernatant removed by aspiration. The DNA pellet was dissolved in 200 μl of a solution of 0.1 M sodium acetate and 0.05 M Tris-HCl, pH=8, and was reprecipitated by the addition of 2 volumes of cold ethanol. After the solution was incubated for 10 minutes at −20° C., the precipitate was collected by centrifugation and constituted the desired plasmid pOW350 DNA. About 1.5 μg of plasmid pOW350 DNA was obtained and suspended in 15 μl of TE buffer (10 mM Tris-HCl, pH=8, and 1 mM EDTA). A restriction site and function map of plasmid pOW350 is presented in FIG. 2 of the accompanying drawings.

B. Construction of Plasmid pOW350-16

About 5 μl (~0.5 μg) of plasmid pOW350 DNA were added to 2 μl of 10X *Eco*RI buffer (1.0 M Tris-HCl, pH=7.5; 0.5 M NaCl; 50 mM MgCl$_2$; and 1 mg/ml bovine serum albumin (BSA)), 12 μl of H$_2$O, and 1 μl (~10 units— all unit definitions herein refer to those of New England Biolabs, 32 Tozer Road, Beverly, Mass. 01915-9990, unless another manufacturer is referenced) of restriction enzyme *Eco*RI. The resulting reaction was incubated at 37° C. for one hour and then terminated by extracting the reaction mixture first with TE-saturated phenol and then with chloroform. The *Eco*RI-digested plasmid pOW350 DNA was precipitated with ethanol and NaOAc, as described above, and then collected by centrifugation. The DNA pellet was resuspended in 5 μl of H$_2$O.

Figure 7:
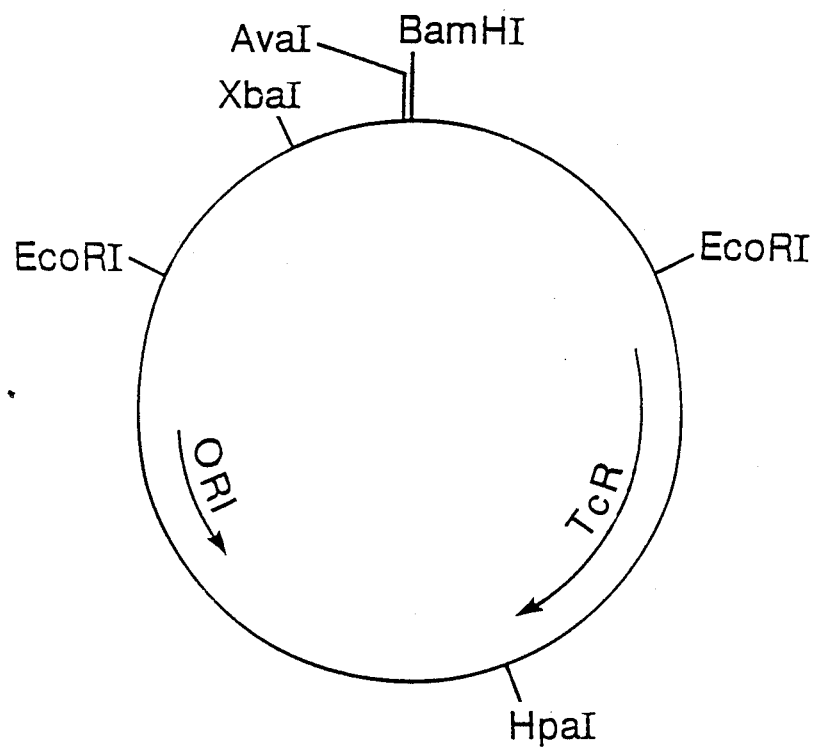
FIG. 7 is a restriction site and function map of plasmid pBC16.

A strain of *Bacillus subtilis* 168/pBC16 was ordered and obtained from the Bacillus Genetic Stock Center, Department of Microbiology, Ohio State University, 484 W. 12th Avenue, Columbus, Ohio 43210, under order number 1E9. The strain was obtained in sporulated form; the spores were spread onto PAB plates (PenAssay broth with 15 g agar/L) containing 10 μg/ml tetracycline to obtain single-colony isolates of *B. subtilis* 168/pBC16. Plasmid pBC16 confers tetracycline resistance to Bacillus host cells; a restriction site and function map of plasmid pBC16 is presented in FIG. 7 of the accompanying drawings. A single colony was picked from the plate and used to inoculate 5 ml of PenAssay broth containing 10 μg/ml of tetracycline. The culture was incubated at 30° C. overnight (~18 hours) with aeration. About 1.0 ml of the culture was removed and used to prepare plasmid pBC16 DNA in substantial accordance with the procedure described in Example 2A. About 1.5 μg of plasmid pBC16 DNA was isolated and resuspended in 15 μl of H$_2$O.

About 5 μl (~0.5 μg) of plasmid pBC16 DNA were digested with restriction enzyme *Eco*RI in substantial accordance with the procedure described for digesting plasmid pOW350 DNA with restriction enzyme *Eco*RI. The *Eco*RI-digested plasmid pBC16 DNA was extracted with phenol and chloroform and precipitated with ethanol and NaOAc, as described above, and then collected by centrifugation. The DNA pellet was resuspended in 5 μl of H$_2$O.

The 5 μl of *Eco*RI-digested plasmid pOW350 DNA were added to the 5 μl of *Eco*RI-digested plasmid pBC16 DNA together with 2 μl of 10X ligase buffer (0.5 M Tris-HCl, pH=7.8; 0.1 M MgCl$_2$; 0.2 M dithiothreitol (DTT); 10 mM ATP; and 500 μg/ml BSA), 1 μl (100 units) of T4 DNA ligase, and 7 μl of H$_2$O, and the resulting reaction was incubated at 16° C. overnight. The ligated DNA constituted the desired plasmid pOW350-16. Plasmid pOW350-16 actually represents two plasmids, for the larger *Eco*RI restriction fragment of plasmid pBC16 DNA could insert into the *Eco*RI site of plasmid pOW350 in either one of two orientations. However, as the orientation of the larger restriction fragment of plasmid pBC16 DNA in plasmid pOW350-16 is irrelevant with respect to the ability of plasmid pOW350-16 to function in Bacillus host cells to drive expression and secretion of nuclease, the plasmids resulting from either orientation were referred to collectively as plasmid pOW350-16. The ligated DNA was used to transform *E. coli* K12 JA221 (NRRL B-15211).

To prepare *E. coli* K12 JA221 cells that are competent for transformation, the lyophils of *E. coli* K12 JA221 obtained from the NRRL are reconstituted on L-agar plates to isolate single colonies. One single-colony isolate of JA221 was inoculated into 5 ml of L broth (10 g of Bacto-tryptone, 10 g of NaCl, and 5 g of Bacto-Yeast Extract, per liter), and the culture was incubated at 37° C. overnight with aeration. Fifty μl of the overnight culture were then used to inoculate 5 ml of L broth, and the culture was again incubated at 37° C. overnight with aeration. The following morning, the culture was diluted to 200 ml with L broth and incubated at 37° C. with aeration until the absorbance at 550 nm (A$_{550}$) was about 0.5, which indicated a cell density of about 1×10$^8$ cells/ml. The culture was cooled for 10 minutes in an ice-water bath, and the cells were then collected by centrifugation at 4000Xg for 10 minutes at 4° C. The cell pellet was resuspended in 100 ml of cold 10 mM NaCl and then immediately collected by centrifugation. The cell pellet was resuspended in 100 ml of 30 mM CaCl$_2$ and incubated on ice for 20 minutes.

The cells were again collected by centrifugation and resuspended in 10 ml of 30 mM CaCl$_2$. A one-half ml aliquot of the cells was added to the ligated DNA prepared above; the DNA had been made 30 mM in CaCl$_2$. The cell-DNA mixture was incubated on ice for 1 hour, heat-shocked at 42° C. for 90 seconds, and then chilled on ice for about 2 minutes. The cell-DNA mixture was diluted with 1 ml of L broth, and one hundred μl aliquots of the mixture were plated on L-agar (L broth with 15 g/l agar) plates containing 100 μg/ml ampicillin. The plates were incubated at 37° C. until colonies appeared. The ampicillin-resistant colonies were patch-tested on L-agar plates containing 10 μg/ml tetracycline, and the test plates were incubated at 37° C. overnight. About 12 of the ampicillin-resistant, tetracycline-resistant colonies were individually inoculated into 5 ml of L-broth containing ampicillin and tetracycline and incubated at 37° C. overnight with aeration. The cultures were used to prepare plasmid DNA in substantial accordance with the procedure of Example 2A. The plasmid DNA of the individual colonies was examined by restriction enzyme analysis and gel electrophoresis to identify the colonies containing the desired plasmid pOW350-16 DNA. Several such colonies were identified, and the plasmid pOW350-16 DNA obtained from these colonies was used to transform *Bacillus subtilis* MI112 as described below.

C. Transformation of *Bacillus subtilis* MI112 with Plasmid pOW350-16

About 50 ml of sterile PAB (Pen Assay broth) were inoculated with *Bacillus subtilis* MI112, which can be obtained from *B. subtilis* MI112/pOW440 (NRRL B-15887) in substantial accordance with the procedure described in Example 5, and incubated at 37° C. with aeration until the cell density reached $2 \times 10^8$ cells/ml. The cells were then protoplasted, using sterile technique, by pelleting and then resuspending the cells in about 5 ml of SMMP (equal volumes of each of 4X PAB and a solution comprising 1 M sucrose, 0.04 M maleic acid, and 0.04 M $MgCl_2$, pH adjusted to 6.5 with NaOH). Next, about 250 $\mu$l of lysozyme (20 mg/ml in SMM [0.5 M sucrose, 0.02 M maleic acid, and 0.02 M $MgCl_2$, pH adjusted to 6.5 with NaOH]) were added using filter sterilization. The cells were incubated with gentle shaking at 37° C. for about 2 hours. The resultant protoplasts were pelleted with centrifugation (25° C., 12 minutes, 2,600 rpm), washed with 5 ml SMMP, and then resuspended in 5 ml SMMP.

About 0.1 ml of protoplasts was transformed by adding about 20 $\mu$l of a 1:1 mixture comprising about 1 $\mu$g plasmid pOW350-16 DNA and 2X SMM. About 1.5 ml of PEG solution (40 g polyethyleneglycol 6000, 50 ml 2X SMMP, and water to 100 ml) were then added followed by about 5 ml of SMMP after about 2 minutes. The protoplasts were then pelleted by centrifugation, suspended in 1 ml of SMMP, and incubated at 30° C. with gentle shaking for about 2 hours. Aliquots of the resultant suspension were plated on DM3 regeneration medium containing 10 $\mu$g/ml tetracycline. DM3 regeneration media contains, per liter, 91 g of D-mannitol, 12 g agar, 50 ml of 10% w/v casamino acids, 50 ml of 10% w/v yeast extract, 25 ml of 20% w/v glucose, 100 ml of 5% w/v dipotassium phosphate, 20 ml of 1 M $MgCl_2$, and 10% w/v gelatin. The D-mannitol, casamino acids and yeast extract were autoclaved together. The gelatin was added immediately after autoclaving, and the remaining ingredients were added after the mixture had cooled.

The regeneration plates were incubated at 37° C. until colonies appeared. Several colonies were picked from the plates and used individually to inoculate 5 ml of Pen Assay broth. The resulting liquid cultures were incubated at 37° C. overnight with aeration and then used to prepare plasmid DNA in substantial accordance with the procedure described in Example 2A. The plasmid DNA was digested with restriction enzymes and the digested DNA electrophoresed on an agarose gel to identify the cultures containing plasmid pOW350-16 DNA. Several *Bacillus subtilis* MI112/pOW350-16 cultures were identified, and nuclease activity in the media was determined as described in Example 4.

EXAMPLE 3

Construction of *Bacillus subtilis* MI112/pOW352-16

A Construction of Plasmid pOW352-16 and *E. coli* K12 JA221/pOW352

To obtain sufficient plasmid pOW350 DNA for use in the construction of plasmid pOW352, the procedure of Example 2A is carried out on a larger scale. About 4 $\mu$g ($\sim$40 $\mu$l) of plasmid pOW350 DNA were added to 10 $\mu$l of 10X HindIII buffer (0.5 M NaCl; 0.5 M Tris-HCl, pH=8.0; 100 mM $MgCl_2$; and 1 mg/ml BSA), 3 $\mu$l ($\sim$30 units) of restriction enzyme HindIII, and 47 $\mu$l of $H_2O$, and the resulting reaction was incubated at 37° C. for 2 hours. The reaction was then extracted plasmid pOW350 DNA was precipitated with NaOAc and ethanol and then resuspended in 9 $\mu$l of $H_2O$. About 1 $\mu$l of loading buffer (25% v/v glycerol, 0.05% w/v bromphenol blue, and 0.05% xylene cyanol) was added to the solution of DNA, which was then electrophoresed on a 1% agarose gel until the desired $\sim$2.67 kb and $\sim$0.54 HindIII restriction fragments were clearly separated from each other.

The electrophoresed DNA was visualized by staining the gel in a dilute solution (0.5 $\mu$g/ml) of ethidium bromide and exposing the stained gel to longwave UV light. After the fragments were located, a small slit was made in the gel in front of each of the desired fragments, and a piece of Schleicher and Schuell (Keene, NH 03431) DEAE membrane was placed in each slit. Upon further electrophoresis, the DNA noncovalently bound to the DEAE membrane. After the desired fragments were bound to the DEAE membrane, the membranes were removed and individually rinsed with low salt buffer (100 mM KCl; 0.1 mM EDTA; and 20 mM Tris-HCl, pH=8). Next, each membrane was individually placed in a small tube and immersed in high salt buffer (1 M NaCl; 0.1 mM EDTA; and 20 mM Tris-HCl, pH=8) and then incubated at 65° C. for 10 minutes to remove the DNA from the DEAE paper. After the 65° C. incubation, the incubation buffer was collected, and the membrane was rinsed with high salt buffer. The rinse solution was pooled with the incubation buffer before collecting the desired DNA fragments.

The volume of the high salt-DNA solutions was adjusted so that the NaCl concentration was 0.25 M, and then three volumes of cold, absolute ethanol were added to each solution. The resulting solutions were mixed and placed at $-70$° C. for 10–20 minutes. The solutions were then centrifuged at 15,000 rpm for 15 minutes. After another precipitation to remove residual salt, the DNA pellets were rinsed with 70% ethanol, dried, resuspended in 20 $\mu$l of TE buffer, and constituted the desired restriction fragments. About 0.6 $\mu$g of the $\sim$0.54 kb fragment was obtained and dissolved in 10 $\mu$l of $H_2O$. About 3 $\mu$g of the $\sim$2.67 kb fragment was obtained and dissolved in 30 $\mu$l of $H_2O$. STOP The solution (10 $\mu$l) of the $\sim$0.54 kb HindIII restriction fragment of plasmid pOW350 was added to 2 $\mu$l of 10X AsuII buffer (200 mM NaCl; 60 mM Tris-HCl, pH=7.4; 60 mM $MgCl_2$; and 60 mM $\beta$-mercaptoethanol), 1 $\mu$l ($\sim$5 units) of restriction enzyme AsuII, and 7 $\mu$l of $H_2O$. The resulting reaction was incubated at 37° C. for 2 hours and then was extracted once with phenol and once with chloroform. Two $\mu$l of loading buffer were added to the reaction mixture, which was then loaded onto a 7% acrylamide gel and electrophoresed until the $\sim$0.46 kb AsuII-HindIII restriction fragment was clearly separated from the $\sim$85 bp AsuII-HindIII restriction fragment. The gel was stained with ethidium bromide, and the gel fragment containing the $\sim$0.46 kb AsuII-HindIII restriction fragment was cut from the gel. The gel fragment was placed in dialysis tubing, which was then sealed and subjected to electrophoresis. The DNA was eluted from the gel by electrophoresis, and then, the solution containing the DNA was collected from the dialysis tubing. The DNA solution was extracted first with phenol and then with chloroform and then 10 was precipitated with ethanol and NaOAc. About 0.4 μg of the ~0.46 kb HindIII-AsuII restriction fragment of plasmid pOW350 was obtained and suspended in 4 μl of H₂O.

The remaining DNA fragment used in the construction of plasmid pOW352 was constructed using an automated phosphite triester method. Although any DNA synthesizer can be used to construct the DNA fragments depicted below, the DNA Synthesizer 380A of Applied Biosystems, Foster City, Calif., is preferred. Those skilled in the art will recognize that the single-stranded DNA molecules can also be synthesized in accordance with the procedure of Itakura et al., 1977, Science 198:1056 and Crea et al., 1978, Proc. Nat. Acad. Sci. USA 75:5765. In addition, an especially preferred synthetic method is disclosed in Hsuing et al., 1983, Nucleic Acid Research 11:3227 and Narang et al., 1980, Methods in Enzymology 68:90. Two single-stranded DNA molecules were synthesized: (1) 5'-AGCTTAGAAAGGAGGTGATCATATGT-3'; and (2) 5'-CGACATATGATCACCTCCTTTCTA-3'.

About 75 picomoles of each single-stranded DNA molecule of the linker were individually dissolved in 22.5 μl of H₂O and 2.5 μl of 10X ligase buffer. About 1 μl (5 units) of T4 DNA kinase was added to each solution of single-stranded DNA, and the reactions were incubated at 37° C. for 10 minutes. Following the kinase reaction, the reaction mixtures were incubated at 70° C. for 15 minutes. Then, to anneal the single-stranded DNA to form the linker, the two reaction mixtures were pooled, incubated at 65° C. for 10 minutes, incubated at room temperature for 2 hours, and then incubated at 4° C. overnight. When annealed, the two strands formed the molecule depicted below:

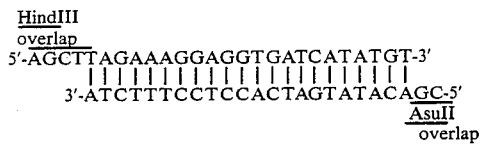

About 5 μl (~0.5 μg) of the ~2.67 kb HindIII restriction fragment of plasmid pOW350 were added to 1 μl (~0.1 μg) of the ~0.46 kb HindIII-AsuII restriction fragment of plasmid pOW350 10 μl (~7.5 picomoles) of the annealed linker, 2 μl of 10X ligase buffer, 1 μl of T4 DNA ligase, and 11 μl of H₂O. The resulting reaction was incubated at 16° C. for 2 hours, and the ligated DNA constituted the desired plasmid pOW352 DNA. A restriction site and function map of plasmid pOW352 is presented in FIG. 3 of the accompanying drawings.

The ligated DNA was used to transform E. coli K12 JA221 in substantial accordance with the procedure described in Example 2B. The transformed cells were plated on L-agar plates containing 100 μg/ml ampicillin; the plates were then incubated at 37° C. overnight (~18 hours). The ampicillin-resistant colonies were patched to nuclease-indicator plates. Nuclease-indicator plates are prepared by dissolving 5 g of NaCl in 450 ml of H₂O, adding 10 ml of 1.0 M Tris-HCl, pH=9.0, adding 30 ml of a 5 mg/ml solution of salmon-sperm DNA (Sigma Chemical Co., P.0. Box 14508, St. Louis, Mo. 63178) in lX SSC (20X SSC is 0.3 M sodium citrate and 3 M NaCl), heating the solution in a microwave until the agar melts, and then adding 10 ml of a toluidine-0-blue (Sigma) solution prepared by dissolving 0.8 g of toluidine-0-blue in 50 ml of H₂O. On nuclease-indicator plates, colonies secreting nuclease form a pink halo around the colony against the otherwise blue background of the plate.

Several nuclease-positive colonies were detected on the indicator plates. Plasmid DNA was isolated from these colonies in accordance with the procedure of Example 2A. The plasmid DNA was subjected to restriction enzyme analysis to identify the E. coli K12 JA221/pOW352 transformants.

B. Construction of Plasmid pOW352-16 and Bacillus subtilis MI112/pOW352-16

Plasmid pOW352-16 was constructed from plasmids pOW352 and pBC16 in substantial accordance with the procedure described in Example 2B, except that plasmid pOW352, rather than plasmid pOW350, was used in the construction. Likewise, Bacillus subtilis Ml112/pOW352-16 cells were constructed from plasmid pOW352-16 and B. subtilis MI112 host cells in substantial accordance with the procedure described in Example 2C, except that plasmid pOW352-16, rather than plasmid pOW350-16, was used in the construction.

EXAMPLE 4

Nuclease Assay

The procedure described below is derived from the nuclease assay of Cuatrecasas et al., 1967, J. Biol. Chem. 242:1541. The "culture" referred to in the procedure represents each individual culture listed in Table I.

About 5 ml of SM media (SM media is Spizizen's minimal media and contains 2% v/v glycerol, 2% w/v casamino acids, and 100 μg/ml L-tryptophan) were inoculated with a single-colony isolate (or 10–100 μl of an overnight culture) of the culture and incubated at 30° C. with aeration. Prior to assay of the culture medium for nuclease activity, the density of the culture was determined using a Klett colorimeter (available from Fisher Scientific, 113 Hartwell Avenue, Lexington, Mass. 02173) with red filter #60. About 2 ml of the culture were removed, and the cells were pelleted by centrifugation. The supernatant was collected and then concentrated and desalted using a Centricon 10 (Amicon, 17 Cherry Hill Dr., Danvers, Mass. 01923) concentrator according to manufacturer's recommendations. The concentration and desalting step reduces the volume of the spent media to 200 μl. Because the nuclease assay is not as accurate when the sample contains high concentrations of nuclease, some samples may require dilution prior to use in the assay. The results presented below were adjusted to account for concentration and reflect units of nuclease per ml of unconcentrated culture media.

About 10 μl of the concentrated and desalted spent media were added to 1 ml of nuclease reaction mixture, which contains 50 μg/ml boiled salmon-sperm DNA; 25 mM borate, pH=8; and 10 mM CaCl₂. The reaction was monitored by plotting the increase in optical density at 260 nm (OD$_{zeo}$) (Y axis) against time (X axis) using a Bausch and Lomb spectrophotomoter 2000 with an X-Y recorder (available from Fisher). Nuclease (Worthington Biochemicals) was used as a standard. As nuclease degrades the DNA present in the reaction mixture, the OD$_{260}$ increases, because the hypoohromioity associated with double-stranded DNA is lost as nuclease degrades the DNA into free nucleotides. The results of the assay are presented in Table I.

TABLE I

| | Nuclease Assay | |
|---|---|---|
| Culture | Optical Density (in Klett units) | Nuclease Activity (U*/ml) |
| B. subtilis MI112/pOW440 | 165 | 22 |
| B. subtilis MI112/pOW350-16 | 165 | 53 |
| B. subtilis MI112/pOW352-16 | 165 | 49 |

*1.0 $\Delta OD_{260}$/minute = 1 U

EXAMPLE 5

Construction of mutant Bacillus subtilis strains with improved expression/secretion abilities for heterologous gene products The following procedure can be used to improve expression of any heterologous (non-Bacillus) gene product in Bacillus subtilis. The procedure is exemplified using plasmid pOW360-16, which encodes a fusion protein of structure: amino terminus-human growth hormone-nuclease-carboxy terminus. The exemplified procedure is therefore structured to obtain B. subtilis mutants with an increased ability to synthesize and secrete human growth hormone. Substituting plasmid pOW362-16 for plasmid pOW360-16 in the following procedure would allow for selection of mutants with an increased ability to synthesize and secrete human proinsulin.

A. Mutagenesis and Screen for Increased Nuclease Activity

A 5 ml culture of Bacillus subtilis MI112/pOW360-16 in PenAssay broth containing 10 μg/ml of tetracycline was incubated at 30° C. with aeration until the culture reached mid-logarithmic growth phase (O.D.$_{600}$ =0.5-0.6). About 200 μl of ethyl methanyl sulfate were added to the culture, and incubation was continued for another 20 minutes. The cells were collected with centrifugation, washed with 5 ml of PenAssay broth, resuspended in 5 ml of PenAssay broth containing 10 μg/ml of tetracycline, and incubated another 5 hours at 30° C. with aeration. The cells were then plated at several different dilutions on PAB plates containing 10 μg/ml tetracycline. The plates were incubated at 37° C. overnight.

Plates containing 100 to 200 colonies/plate were replica-plated onto nuclease-indicator plates, which were then incubated at 37° C. overnight. Several colonies, which will be referred to as hypersecretors, indicated increased nuclease secretion, as determined by the size of the halo around the colony caused by degradation of the DNA-agar-toluidine-O-blue complex. To determine if the increased nuclease production resulted from a mutation in the chromosomal, as opposed to plasmid, DNA of the cell, the cells exhibiting increased nuclease production were cured of plasmid and then retransformed with plasmid pOW360-16.

The hypersecretors were cured of plasmid DNA by protoplasting and then regenerating the cells as in the transformation protocol described in Example 2C. During regeneration, however, no antibiotic was added to the regeneration media, because the purpose of the protoplasting and regeneration was to cause the cells to lose the plasmid DNA responsible for the tetracycline-resistant phenotype. After regeneration, the cells were patch-tested to tetracycline-containing PAB plates; the tetracycline-sensitive cells were determined free of plasmid DNA.

The hypersecretor cell lines, cured of plasmid DNA, were then retransformed with plasmid pOW360-16 in substantial accordance with the procedure of Example 2C. The transformed cells were identified by their tetracycline-resistant, nuclease-positive phenotype. Table II, below, demonstrates that the hypersecretor strains (HI and HII) have a greater ability to synthesize and secrete the HGH fusion polypeptide encoded on plasmid pOW360-16.

TABLE II

| | Increased Nuclease Activity Produced by Hypersecretor Strains | | |
|---|---|---|---|
| Strain | Plasmid | (Klett Units) Optical Density | Nuclease Activity (U/ml) |
| B. subtilis 168* | pOW360-16 | 165 | 5.0 |
| HI | pOW360-16 | 165 | 17.3 |
| HII | pOW360-16 | 165 | 18.0 |
| B. subtilis 168 | pOW350-16 | 165 | 52.5 |
| HI | pOW350-16 | 165 | 200 |
| HII | pOW350-16 | 165 | 189 |

*Bacillus subtilis 168 can be obtained from the Bacillus Genetic Stock Center, order #1A1.

The hypersecretor cell lines prepared in Example 5A were transformed with plasmid pOW885-16 in substantial accordance with the procedure of Example 2C. The regenerated, transformed cells were transferred to SM media to determine HGH secretion. SM media is preferred, because higher secretion rates are observed for Bacillus subtilis strains in minimal media. The cells were grown to an optical density of 165 Klett units, and about 1.5 ml of the culture were removed, the d, and the media concentrated to 200 μl using the Centricon 10 concentration/desalination apparatus. About 20 μl of the concentrated media were added to 2 μof loading buffer, and then, the sample was electrophoresed on a 14% SDS-polyacrylamide gel. Whereas wild-type Bacillus subtilis MI112/pOW885-16 cells produce no detectable HGH under the conditions described above, the hypersecretor strains do produce HGH.

We claim

1. A recombinant DNA vector that comprises the DNA sequence

```
5'-AATTCTAGT  TATTTTATTA  TAATTATTAA
   |||||      ||||||||||  ||||||||||
3'-GATCA      ATAAAATAAT  ATTAATAATT

ATTTTTATTA  ATTAATTGAC  AAAATGTAGA
   ||||||||||  ||||||||||  ||||||||||
   TAAAAATAAT  TAATTAACTG  TTTTACATCT

ATTATAATTA  TAATACGTTT  AATATTAAAA
   ||||||||||  ||||||||||  ||||||||||
   TAATATTAAT  ATTATGCAAA  TTATAATTTT

TTA-3'
                           |||
                           AATTCGA-5'
``` wherein A is deoxyadenyl, G is deoxyguanyl, C is deoxycytidyl, and T is thymidyl.

2. A recombinant DNA vector that codes for expression of a gene product that contains the functional signal peptide:

| | | | | | | | | | | | | |
|---|---|---|---|---|---|---|---|---|---|---|---|---|
| MET | THR | GLU | TYR | LEU | LEU | SER | ALA | GLY | ILE | CYS | MET | ALA ILE VAL |
| SER | ILE | LEU | LEU | ILE | GLY | MET | ALA | ILE | SER | ASN | VAL | SER LYS GLY |
| GLN | TYR | ALA | LYS | ARG | PHE | PHE | PHE | PHE | ALA | THR | SER | CYS LEU VAL |
| LEU | THR | LEU | VAL | VAL | VAL | SER | SER | LEU | SER | SER | SER | ALA ASN ALA | wherein ALA is alanine, ARG is arginine, ASN is asparagine, ASP is aspartic acid, CYS is cysteine, GLN is glutamine, GLU is glutamic acid, GLY is glycine, HIS is histidine, ILE is isoleucine, LEU is leucine, LYS is lysine, MET is methionine, PHE is phenylalanine, PRO is proline, SER is serine, THR is threonine, TRP is tryptophan, TYR is tyrosine, and VAL is valine, and wherein one or more of the residues from position 2 (threonine) up to position 28 (serine) have been deleted.

3. The recombinant DNA vector of claim 2 that codes for expression of a gene product that contains the signal peptide:

| | | | | | | | | | | |
|---|---|---|---|---|---|---|---|---|---|---|
| MET | ALA | ILE | CYS | MET | ALA | ILE | VAL | SER | ILE | LEU LEU ILE |
| GLY | MET | ALA | ILE | SER | ASN | VAL | SER | LYS | GLY | GLN TYR ALA |
| LYS | ARG | PHE | PHE | PHE | PHE | ALA | THR | SER | CYS | LEU VAL LEU |
| THR | LEU | VAL | VAL | VAL | SER | SER | LEU | SER | SER | SER ALA ASN ALA | wherein ALA is alanine, ARG is arginine, ASN is asparagine, ASP is aspartic acid, CYS is cysteine, GLN is glutamine, GLU is glutamic acid, GLY is glycine, HIS is histidine, ILE is isoleucine, LEU is leucine, LYS is lysine, MET is methionine, PHE is phenylalanine, PRO is proline, SER is serien, THR is threonine, TRP is tryptophan, TYR is tyrosine, and VAL is valine.

4. The recombinant DNA vector of claim 2 that codes for expression of a gene product that contains the signal peptide:

| | | | | | | | | |
|---|---|---|---|---|---|---|---|---|
| MET | SER | LYS | GLY | GLN | TYR | ALA | LYS | ARG PHE PHE PHE |
| PHE | ALA | THR | SER | CYS | LEU | VAL | LEU | THR LEU VAL VAL |
| VAL | SER | SER | LEU | SER | SER | SER | ALA | ASN ALA | wherein ALA is alanine, ARG is arginine, ASN is asparagine, ASP is aspartic acid, CYS is cysteine, GLN is glutamine, GLU is glutamic acid, GLY is glycine, HIS is histidine, ILE is isoleucine, LEU is leucine, LYS is lysine, MET is methionine, PHE is phenylalanine, PRO is proline, SER is serine, THR is threonine, TRP is tryptophan, TYR is tyrosine, and VBAL is valine.

5. The recombinant DNA vector of claim 1 that is a plasmid.
6. The plasmid of claim 5 that is plasmid pOW350.
7. The plasmid of claim 5 that is plasmid pOW352.
8. The plasmid of claim 5 that is plasmid pOW885.
9. The plasmid of claim 5 that is plasmid pOW350-16.
10. The plasmid of claim 5 that is plasmid pOW352-16.
11. The plasmid of claim 5 that is plasmid pOW885-16.
12. The plasmid of claim 5 that is selected from the group comprising pOW350, pOW352, pOW885, pOW350-16, pOW352-16, pOW885-16.
13. The vector of claim 5 that is plasmid pOW360.
14. The vector of claim 5 that is plasmid pOW360-16.
15. A recombinant host cell selected from the group consisting of E. coli and Bacillus transformed with a plasmid of claim 12.
16. A recombinant host cell selected from the group consisting of E. coli and Bacillus transformed with a vector of claim 1.
17. The recombinant host cell of claim 16 that is E. coli K12.
18. The recombinant host cell of claim 16 that is Bacillus subtilis.
19. The recombinant host cell of claim 15 that is E. coli K12 JA221/pOW350.
20. The recombinant host cell of claim 15 that is E. coli K12 JA221/pOW352.
21. The recombinant host cell of claim 15 that is E. coli K12 JA221/pOW885.
22. The recombinant host cell of claim 15 that is Bacillus subtilis MI112/pOW352-16.
23. The recombinant host cell of claim 15 that is Bacillus subtilis MI112/pOW885-16.
24. The recombinant host cell of claim 15 that is Bacillus subtilis MI112/pOW350-16.

* * * * *